US011433120B2

(12) United States Patent
Tiberg et al.

(10) Patent No.: US 11,433,120 B2
(45) Date of Patent: *Sep. 6, 2022

(54) CONTROLLED RELEASE PEPTIDE FORMULATIONS

(75) Inventors: Fredrik Tiberg, Lund (SE); Catalin Nistor, Lund (SE); Markus Johnsson, Lund (SE)

(73) Assignee: CAMURUS AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/117,994

(22) PCT Filed: May 25, 2012

(86) PCT No.: PCT/EP2012/059917
§ 371 (c)(1),
(2), (4) Date: Feb. 20, 2014

(87) PCT Pub. No.: WO2012/160213
PCT Pub. Date: Nov. 29, 2012

(65) Prior Publication Data
US 2014/0162944 A1    Jun. 12, 2014

Related U.S. Application Data

(60) Provisional application No. 61/489,886, filed on May 25, 2011.

(51) Int. Cl.
| *A61K 38/31* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/655* | (2006.01) |
| *A61K 9/00* | (2006.01) |
| *A61K 47/10* | (2017.01) |
| *A61K 9/127* | (2006.01) |
| *A61K 47/14* | (2017.01) |
| *A61K 47/24* | (2006.01) |
| *A61K 38/00* | (2006.01) |

(52) U.S. Cl.
CPC ............ *A61K 38/31* (2013.01); *A61K 9/0019* (2013.01); *A61K 9/0024* (2013.01); *A61K 9/1274* (2013.01); *A61K 47/10* (2013.01); *A61K 47/14* (2013.01); *A61K 47/24* (2013.01); *C07K 14/655* (2013.01); *A61K 38/00* (2013.01)

(58) Field of Classification Search
None
See application file for complete search history.

(56) References Cited

U.S. PATENT DOCUMENTS

| 8,097,239 B2* | 1/2012 | Johnsson et al. ............. 424/9.2 |
| 8,236,292 B2* | 8/2012 | Thuresson et al. .......... 424/85.7 |
| 8,545,832 B2* | 10/2013 | Thuresson et al. .......... 424/85.7 |
| 8,546,326 B2* | 10/2013 | Joabsson et al. ............... 514/7.2 |
| 8,865,021 B2* | 10/2014 | Joabsson et al. ........ 252/299.01 |
| 9,555,118 B2* | 1/2017 | Tiberg .................. A61K 9/0024 |
| 9,585,959 B2* | 3/2017 | Tiberg .................. A61K 9/0024 |
| 9,668,967 B2* | 6/2017 | Nistor .................. A61K 9/0024 |
| 2008/0274176 A1* | 11/2008 | Johnsson et al. ............. 424/463 |
| 2009/0155193 A1 | 6/2009 | Joabsson et al. |
| 2009/0170782 A1* | 7/2009 | Joabsson et al. ............... 514/15 |
| 2010/0210519 A1* | 8/2010 | Johnsson et al. ............... 514/11 |
| 2011/0230569 A1* | 9/2011 | Nistor et al. ................... 514/777 |
| 2014/0193347 A1* | 7/2014 | Thuresson et al. ............. 424/52 |
| 2014/0329749 A1* | 11/2014 | Tiberg et al. ................ 514/11.1 |
| 2014/0348903 A1* | 11/2014 | Tiberg et al. ................. 424/450 |
| 2015/0064118 A1* | 3/2015 | Thuresson et al. ............. 424/52 |
| 2015/0105332 A1* | 4/2015 | Nistor et al. ................. 514/21.1 |

FOREIGN PATENT DOCUMENTS

| CN | 101035511 A | 9/2007 | |
| WO | 2005117830 A1 | 12/2005 | |
| WO | 2006/013369 A2 | 2/2006 | |
| WO | 2006/075124 A1 | 7/2006 | |
| WO | 2006/131730 A1 | 12/2006 | |
| WO | WO 2006131730 A1 * | 12/2006 | ............... A61K 9/10 |
| WO | 2009/024795 A1 | 2/2009 | |

(Continued)

OTHER PUBLICATIONS

U.S. Appl. No. 14/595,852 filed Jan. 2015, Johnsson et al.*
Pharmaceutics and Compounding Laboratory, available online at http://pharmlabs.unc.edu/labs/solubility/structure.htm, 3 pages (first available 2008).*
TutoVista.com, "Solvents", available online at http://chemistry.tutorvista.com/inorganic-chemistry/solvent.html, 4 pages (accessed on Nov. 13, 2017) (Year: 2017).*
Rowe et al., eds., Handbook of Pharmaceutical Excipients, 6th Ed., Pharmaceutical Press and American Pharmacists Association, pp. 1-27 and 592-594 (2009) (Year: 2009).*

(Continued)

*Primary Examiner* — Thea D'Ambrosio
(74) *Attorney, Agent, or Firm* — J.A. Lindeman & Co. PLLC

(57) ABSTRACT

The present invention relates to compositions forming a low viscosity mixture of: a) 20-80 wt. % of at least one diacyl glycerol and/or a tocopherol; b) 20-80 wt. % of at least one phosphatidyl choline (PC); c) 5-20 wt. % of at least one biocompatible, organic mono-alcoholic solvent; d) up to 20 wt. % polar solvent e) at least one peptide active agent; f) optionally at least one antioxidant; wherein the ratio of components a:b is in the range 40:60 to 54:46; wherein the pre-formulation forms, or is capable of forming, at least one liquid crystalline phase structure upon contact with excess aqueous fluid. The invention further relates to methods of treatment comprising administration of such compositions, and to pre-filled administration devices and kits containing the formulations.

28 Claims, 5 Drawing Sheets
Specification includes a Sequence Listing.

(56) References Cited

FOREIGN PATENT DOCUMENTS

| WO | WO 2009024795 A1 | * | 2/2009 | ........... A61K 9/0019 |
| WO | WO 2010020794 A1 | * | 2/2010 | ........... A61K 9/0024 |

OTHER PUBLICATIONS

Patel et al., BioProcess Intl., available online at https://bioprocessintl.com/manufacturing/formulation/biopharmaceutical-product-stability-considerations-part-1/, 16 pages (Jan. 2011) (Year: 2011).*
Rowe et al., eds., Handbook of Pharmaceutical Excipients, 6th Ed., pp. 247-250 (2009) (Year: 2009).*
PubChem Database, Octreotide, available online https://pubchem.ncbi.nlm.nih.gov/compound/Octreotide, 42 pages (first available 2005) (Year: 2005).*
Modlin et al., Aliment Pharmacol. Ther. 31:169-188 (2009) (Year: 2009).*
International Search Report for International Application No. PCT/EP2012/059917, dated Aug. 14, 2012.
International Preliminary Report on Patentability for International Application No. PCT/EP2012/059917, dated Nov. 26, 2013.

* cited by examiner

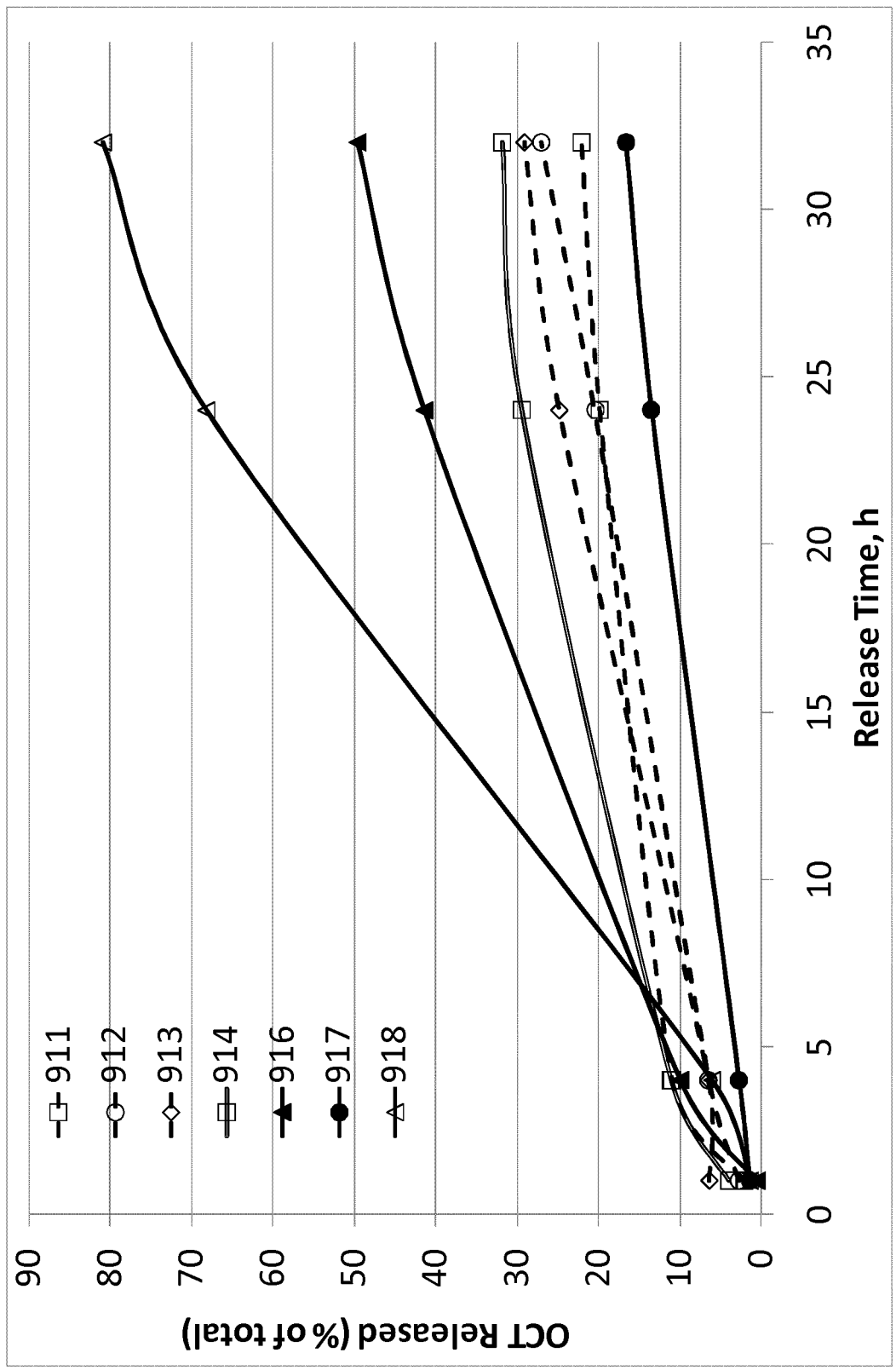
Figure 1a. IVR profile of formulations 911 to 918.

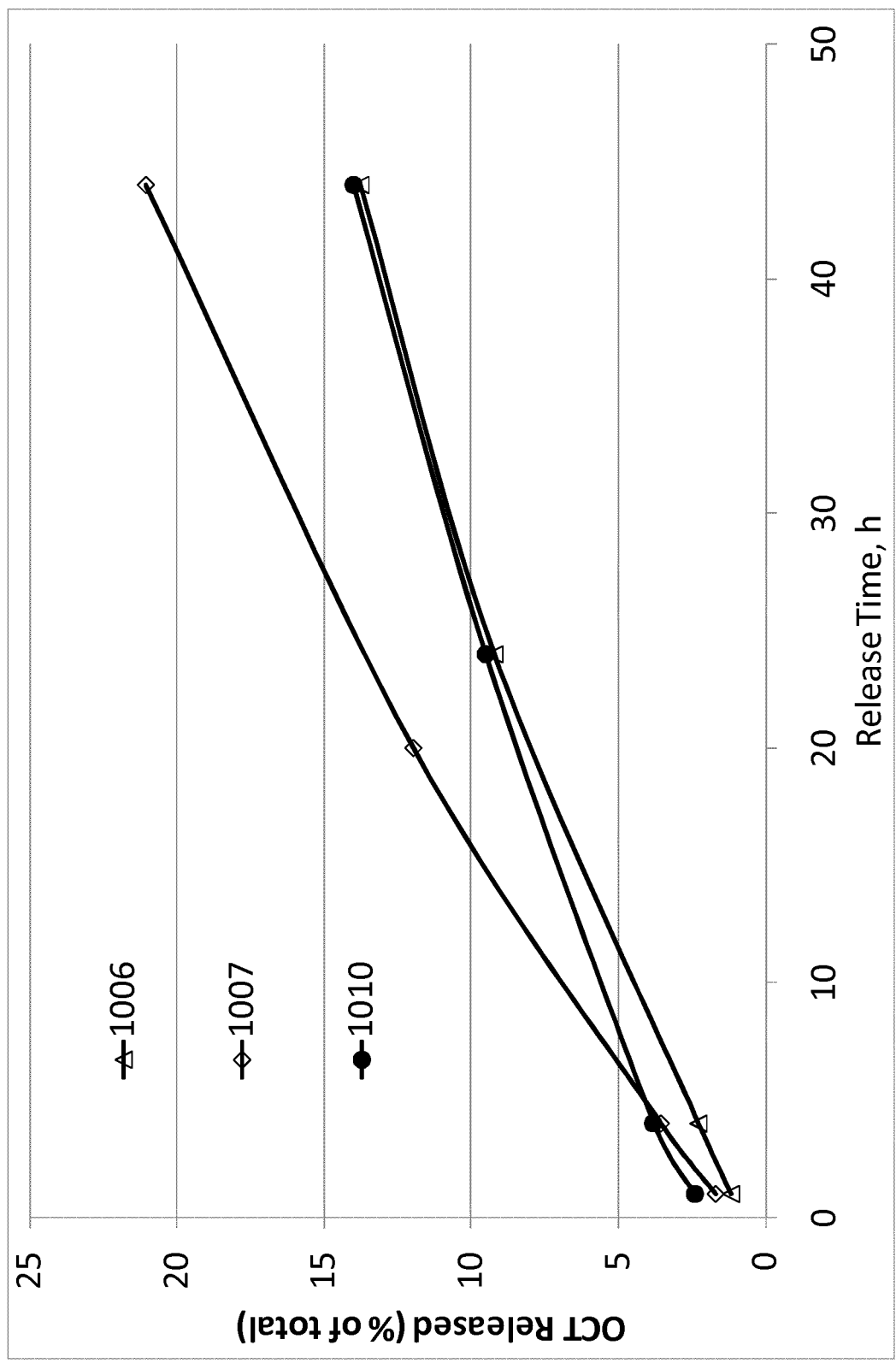
Figure 1b. IVR profile of formulations 1006, 1007, and 1010.

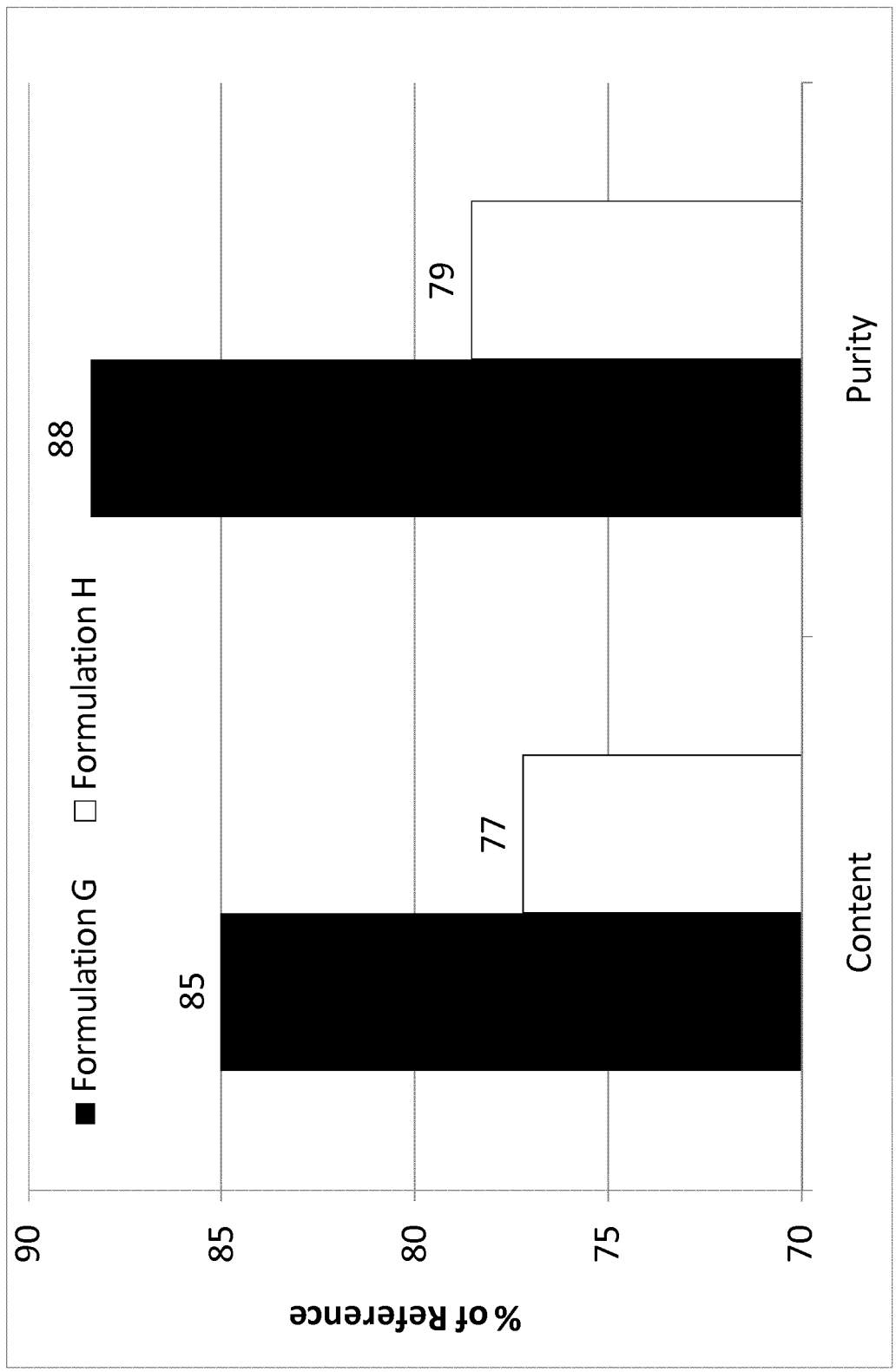
Figure 2: Peptide Content and Purity after storage of formulations G and H for 7 days at 70°C.

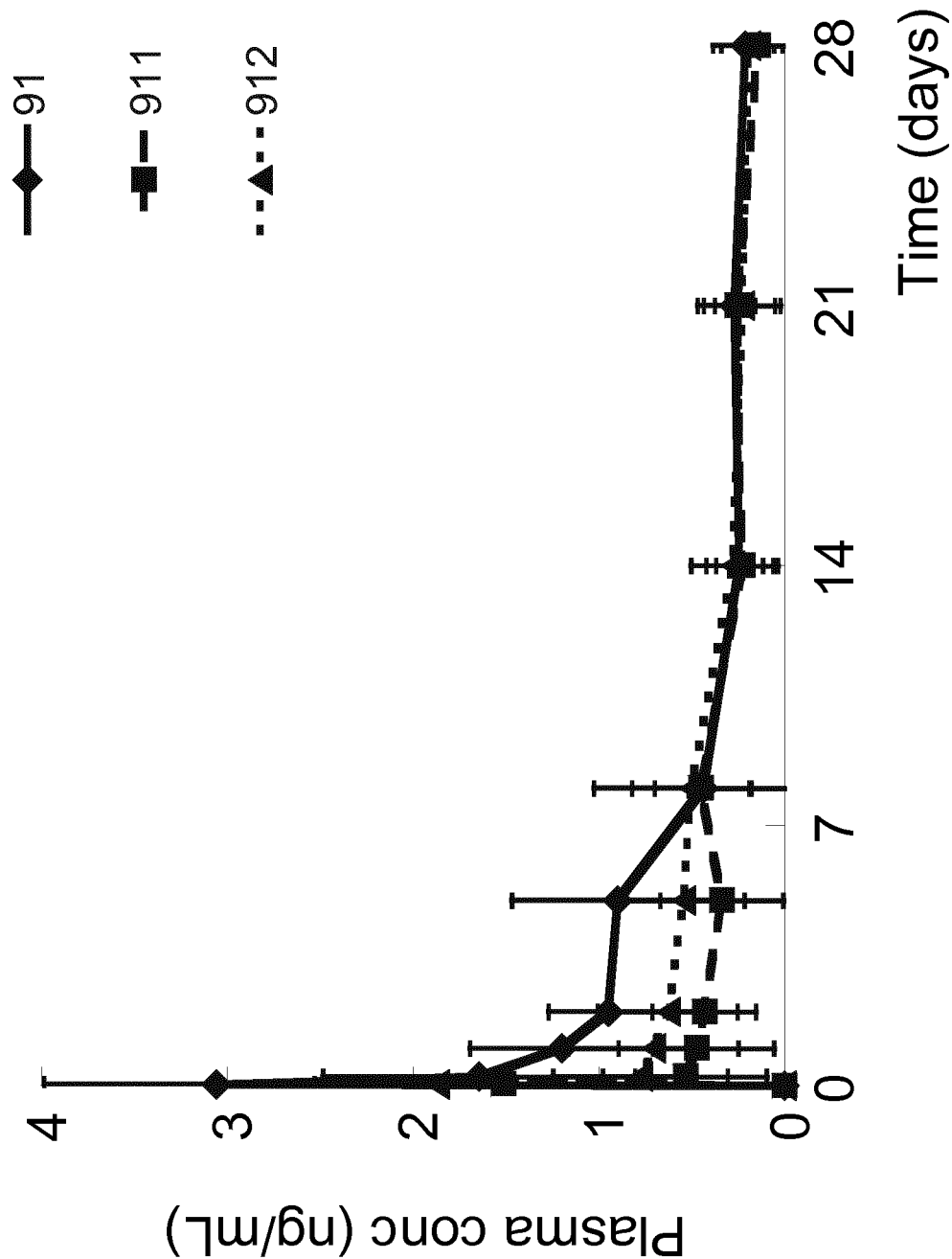
Figure 3. PK-11-413, dose normalized

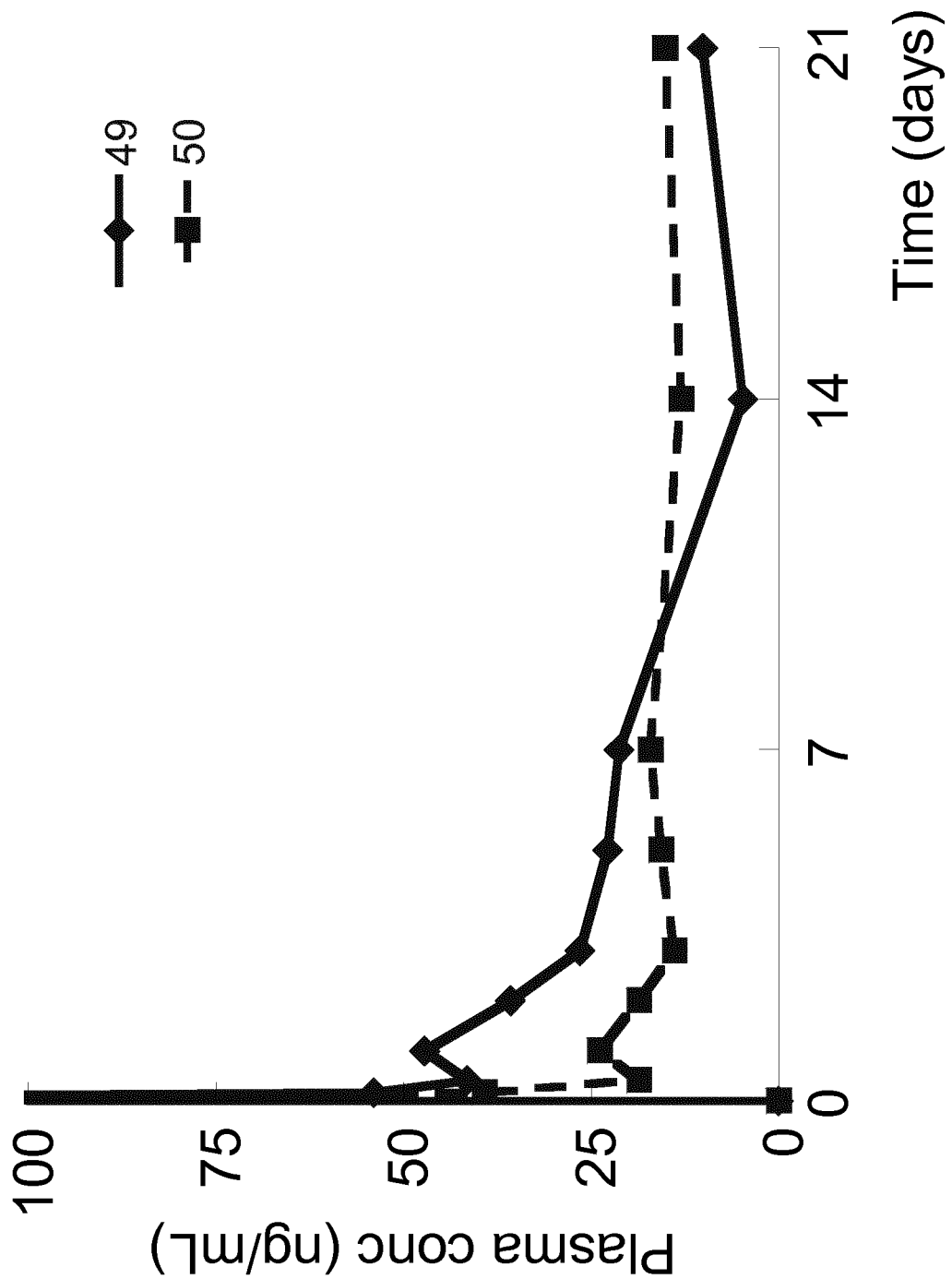
Figure 4. PK-11-425, leuprolide plasma concentration versus time over 21 days for formulation 49 and 50, respectively.

CONTROLLED RELEASE PEPTIDE FORMULATIONS

FIELD OF THE INVENTION

The present invention relates to formulation precursors (pre-formulations) for the in situ generation of compositions for the controlled release of peptide active agents, and methods of treatment with such formulations. In particular, the invention relates to high-loading pre-formulations of amphiphilic components and at least one peptide active agent for parenteral application, which undergo phase transition upon exposure to aqueous fluids, such as body fluids, thereby forming a controlled release composition.

BACKGROUND TO THE INVENTION

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

There is an enormous potential in the use of peptides (including proteins) for treating various disease states, as well as in prophylaxis and in improving general health and well-being of subjects. However, the performance of administered peptide agents is generally limited due to poor bioavailability, which in turn is caused by the rapid degradation of peptides and proteins in biological fluids. This increases the dose which must be administered and in many cases restricts the effective routes of administration. These effects are further exaggerated by the often limited permeability of peptides and proteins across biological membranes.

Peptides and proteins that are administered to the mammalian body (e.g. orally, intramuscularly etc.) are subject to degradation by various proteolytic enzymes and systems present throughout the body. Well known sites of peptidase activity include the stomach (e.g. pepsin), and the intestinal tract (e.g. trypsin, chymotrypsin, and others) but other peptidases (e.g. aminopeptidases, carboxypeptidases, etc.) are found throughout the body. Upon oral administration, gastric and intestinal degradation reduces the amount of peptide or protein which potentially could be absorbed through the intestinal surface lining and thereby decreases their bioavailability. Similarly, free peptides and proteins in the mammalian blood stream are also subject to enzymatic degradation (e.g. by plasma proteases etc.).

Some patients undergoing treatment will typically require a therapeutic dose to be maintained for a considerable period and/or ongoing treatment for many months or years. Thus a depot system allowing loading and controlled release of a larger dose over a longer period would offer a considerable advantage over conventional delivery systems.

Peptides may be delivered by systems such as the Alkermes Medisorb® delivery system consisting of microspheres of biodegradable polymers. Such polymer microsphere formulations must generally be administered by means of a sizable needle, typically of 20-gauge or wider. This is necessary as a result of the nature of the polymeric dosing systems used, which are typically polymer suspensions.

Evidently, it would be an advantage to provide a system of low viscosity, such as a homogeneous solution, dispersion of fine particles, or $L_2$ phase, which could be administered easily through a narrow needle, thus decreasing the discomfort of the patient during the procedure. This ease of administration is particularly significant where patients will be on a self-administration regime and may already be self-administering several times each day. Providing a sustained formulation with a duration of a few days, but which is sufficiently complex to administer that it requires treatment by a healthcare professional will not be an advantage to all patients over twice-daily or daily self-administration, and is likely to be more costly. Providing a formulation which gives sufficiently long duration to justify a visit to a health professional for administration and/or a preparation which can be self-administered, and reducing preparation time of health-care professionals or patients prior to the actual administration are all important issues.

The poly-lactate, poly-glycolate and poly-lactate-co-glycolate polymers typically used for degrading slow-release formulations are also the cause of some irritation in at least some patients. In particular, these polymers typically contain a certain proportion of acetic acid impurity, which will irritate the injection site on administration. When the polymer then breaks down, lactic acid and glycolic acid are the degradation products so that further irritation is caused. As a result of the combined effects of wide-needle administration and irritant contents, discomfort at the site of administration and the formation of connective scar tissue are greater than desirable.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration for a period of time. Evidently, from a functional and toxicological point of view this burst/lag release profile is undesirable and could be dangerous. It may also limit the equilibrium concentration which can be provided due to the danger of adverse effects at the "peak" point. The presence of a lag phase may furthermore require supplementary dosing with repeat injections during the start-up period of depot treatment in order to maintain a therapeutic dose while the concentrations of active provided from the depot are sub-functional. For certain polypeptides in particular, it would be advantageous to minimise the immediate "burst" effect upon administration of a composition in order to avoid side effects such as hypoglycaemia.

One class of peptide hormones which benefits particularly from a very "low burst", stable in vivo concentration are Somatostatin analogues. In vivo testing suggests that these peptides are particularly beneficial when maintained at a steady plasma concentration. This not only suggests that a depot composition would be an advantage to avoid "spikes" in concentration upon administration and/or repeated daily dosing, but furthermore that such a depot composition should have as flat a release profile as possible during the therapeutic period.

Controlled-release formulations are typically generated from bio-compatible polymers in the form of, for example, implants or injectable beads. Polymer microsphere formulations must generally be administered by means of a sizable needle, typically of 20-gauge or wider. This is necessary as a result of the nature of the polymeric dosing systems used, which are typically polymer suspensions. It would be an advantage to provide a system of low viscosity, such as a homogeneous solution, dispersion of fine particles, or $L_2$ phase, which could be administered easily through a narrow needle, thus decreasing the discomfort of the patient during the procedure. In the case of diabetic patients, whether for daytime or nightly use, this ease of administration is particularly significant because most patients will be frequently self-administering. Providing a sustained formulation which can prevent or reduce the risk of hypoglycemia (especially nocturnal hypoglycemia), but which is sufficiently complex to administer that it requires treatment by a healthcare professional is unlikely to be successful, because the lifestyle disruption involved with such complex administrations, as well as the costs involved would be too great. Providing a formulation which can be self-administered, and which is sufficiently straightforward and painless to administer that patient compliance is not adversely affected is greatly needed for such situations.

The manufacture of PLGA microbeads and suspensions is additionally a considerable difficulty with certain existing depot systems. In particular, since the beads are particulate, and polymers clog membranes, they cannot generally be sterile-filtered and furthermore, since the PLGA copolymer melts at around 40° C., they cannot be heat-treated for sterility. As a result, a complex manufacturing process must all be conducted under conditions of high sterility.

Further issues with biodegradable polymer microspheres include complex reconstitution prior to injection and limited storage stability, due both to aggregation and degradation of the delivery system and/or active.

A lipid-based, slow-release composition is described in WO2006/131730 for GLP-1 and analogues thereof. This is a highly effective formulation, but the concentration of active agent which can be included in the formulation is limited by its solubility. Evidently, a higher concentration of active agent allows for the possibility of longer duration depot products, products maintaining a higher systemic concentration, and products having a smaller injection volume, all of which factors are of considerable advantage under appropriate circumstances. It would thus be of considerable value to establish a way by which higher concentrations of active agents could be included in a lipid-based depot formulation.

The present inventors have now established that by providing a pre-formulation comprising at least one neutral diacyl glycerol and/or a tocopherol, at least one phosphatidyl choline, at least one biocompatible organic mono-alcoholic solvent, at least one polar solvent, at least one peptide active agent and optionally at least one antioxidant in a low viscosity phase, such as molecular solution or $L_2$ (reversed micellar) phase, a pre-formulation may be generated addressing many of the shortfalls of known depot formulations, and which may be applied to provide a controlled release of peptide active agent. By use of specific components in carefully selected ratios, and in particular with a mixture of an alcohol and a polar solvent, a depot formulation can be generated having a combination of properties exceeding the performance of even the known lipid controlled-release compositions.

In particular, the pre-formulation shows a highly advantageous release profile, is easy to manufacture, may be sterile-filtered, has low viscosity (allowing easy and less painful administration typically through a narrow needle), allows a high level of bioactive agent to be incorporated (thus potentially allowing a smaller amount of composition and/or active agent to be used), requires shallow injection and/or forms a desired non-lamellar depot composition in vivo having a "non-burst" release profile. The compositions are also formed from materials that are non-toxic, biotolerable and biodegradable, which can be administered by i.m., or s.c. and are suitable for self-administration. The pre-formulation may additionally have a very low level of irritation on injection and in preferred cases causes no irritation at the injection site (including transient irritation).

Certain of the formulations of the present invention generate a non-lamellar liquid crystalline phase following administration. The use of non-lamellar phase structures (such as liquid crystalline phases) in the delivery of bioactive agents is now relatively well established. A most effective lipid depot system is described in WO2005/117830, and a highly preferred lipid depot is described in that document. However, there remains scope for achieving depot formulations having improved performance in several respects.

Advantages of the compositions of the present invention over polymer formulations, such as PLGA spheres, include the ease of manufacture (including sterilization), handling and use properties combined with low initial release ("non-burst profile") of active agent. This may be defined such that the area under a plasma concentration against time the curve during the first 24 hours of a one-month dosing period is less than 20% of the area under the curve for the entire curve (measured or extrapolated from time 0 to infinity or from time 0 to the last sampling time point), more preferably less than 15% and most preferable less than 10%. This applies particularly to the acyl saccharide and lipid aspects of the invention and is discussed in more detail in WO 2005/117830. Furthermore, it may be defined such that the maximum plasma concentration of active agent in vivo following injection of the pre-formulation (Cmax) is no more than 10 times, preferably no more than 8 times and most preferably no more than 5 times the average plasma concentration during the therapeutic period (Cave).

SUMMARY OF THE INVENTION

The present invention provides a pharmaceutical formulation comprising an appropriate combination of lipid excipients, organic alcoholic solvent, polar solvent, peptide active agent and certain optional components, that can be used as a depot-precursor formulation (referred to herein for brevity as a pre-formulation) to address one or more of the needs described above.

In a first aspect, the invention therefore provides a pre-formulation comprising a low viscosity mixture of:
 a. 20-80 wt. % of at least one diacyl glycerol and/or a tocopherol;
 b. 20-80 wt. % of at least one phosphatidyl choline (PC);
 c. 5-20 wt. % of at least one biocompatible, organic mono-alcoholic solvent;
 d. up to 20 wt. % polar solvent
 e. at least one peptide active agent;
 f. optionally at least one antioxidant;
wherein the ratio of components a:b is in the range 40:60 to 54:46;
wherein the pre-formulation forms, or is capable of forming, at least one liquid crystalline phase structure upon contact with excess aqueous fluid.

Such compositions will preferably comprise GDO, ethanol, water/propylene glycol and/or EDTA as components a), c), d) and f) respectively. Component e) is preferably at least one somatostatin analogue, as described herein.

In a second embodiment, the invention correspondingly provides a process for the formation of a pre-formulation suitable for the administration of a peptide bioactive agent to a (preferably mammalian) subject, said process comprising forming a low viscosity mixture of:
 a) 20-80 wt. % of at least one diacyl glycerol and/or a tocopherol;
 b) 20-80 wt. % of at least one phosphatidyl choline (PC);
 c) 5-20 wt. % of at least one biocompatible, organic mono-alcoholic solvent;
 d) up to 20 wt. % polar solvent
 e) at least one peptide active agent;
 f) optionally at least one antioxidant;
wherein the ratio of components a:b is in the range 40:60 to 54:46;
and dissolving or dispersing at least one peptide active agent (preferably a somatostatin analogue) in the low viscosity mixture, or in at least one of components a), b), c), d) and optionally f) prior to forming the low viscosity mixture. Such a pre-formulation will typically be one as described herein.

The preformulations are highly useful for the controlled and sustained release of peptide active, especially those requiring or benefiting from a very flat release profile and/or minimal "burst" upon administration. In a corresponding embodiment, the invention therefore provides for the use of a low viscosity mixture of:
 a) 20-80 wt. % of at least one diacyl glycerol and/or a tocopherol;
 b) 20-80 wt. % of at least one phosphatidyl choline (PC);
 c) 5-20 wt. % of at least one biocompatible, organic mono-alcoholic solvent;
 d) up to 20 wt. % polar solvent
 e) at least one peptide active agent;
 f) optionally at least one antioxidant;
wherein the ratio of components a:b is in the range 40:60 to 54:46;
in the manufacture of a pre-formulation for use in the sustained administration of said peptide active agent. Such a low viscosity mixture will preferably be one described herein.

The peptide active agents in the formulations of the present invention are preferably pharmaceutically active. That is to say that they provide a therapeutic, palliative and/or prophylactic effect when administered to a suitable subject (typically being one in need of such an effect). IN a further embodiment, the invention therefore provides a method for the treatment of a human or non-human mammalian subject comprising administering to said subject a pre-formulation as described herein.

Such a method may be for the treatment of a human or non-human mammalian subject in need thereof to combat, (e.g. cure, improve, prevent or ameliorate the symptoms of) at least one condition selected from acromegaly, cancers, carcinomas, melanomas, tumours expressing at least one somatostatin receptor, sst(2)-positive tumours, sst(5)-positive tumours, prostate cancers, gastro-entero-pancreatic neuroendocrine (GEP NE) tumours, carcinoid tumours, insulinomas, gastrinomas, vasoactive intestinal peptide (VIP) tumours and glucagonomas, elevated growth hormone (GH), elevated insulin-like growth factor I (IGF-I), varicial bleeding (especially esophageal), chemotherapy induced gastro intestinal problems (such as diarrhea), lymphorrhea, diabetic retinopathy, thyroid eye disease, obesity, pancreatitis, and related conditions. Such methods are particularly applicable where component e) is at least one somatostatin analogue, as described herein. The preformulations as described herein for use in such methods form a further aspect of the invention.

Correspondingly, in a further aspect, the present invention provides the use of a low viscosity mixture of:
 a) 20-80 wt. % of at least one diacyl glycerol and/or a tocopherol;
 b) 20-80 wt. % of at least one phosphatidyl choline (PC);
 c) 5-20 wt. % of at least one biocompatible, organic mono-alcoholic solvent;
 d) up to 20 wt. % polar solvent
 e) at least one peptide active agent;
 f) optionally at least one antioxidant;
wherein the ratio of components a:b is in the range 40:60 to 54:46;
in the manufacture of a low viscosity pre-formulation medicament for use in the in vivo formation of a depot for treatment of at least one condition selected from acromegaly, cancers, carcinomas, melanomas, tumours expressing at least one somatostatin receptor, sst(2)-positive tumours, sst(5)-positive tumours, prostate cancers, gastro-entero-pancreatic neuroendocrine (GEP NE) tumours, carcinoid tumours, insulinomas, gastrinomas, vasoactive intestinal peptide (VIP) tumours and glucagonomas, elevated growth hormone (GH), elevated insulin-like growth factor I (IGF-I), varicial bleeding (especially esophageal), chemotherapy induced gastro intestinal problems (such as diarrhea), lymphorrhea, diabetic retinopathy, thyroid eye disease, obesity, pancreatitis, and related conditions. Such uses are particularly applicable where component e) is at least one somatostatin analogue, as described herein.

Certain peptide active agents have benefits which are cosmetic rather than (or in addition to) therapeutic in nature. Such effects include weight-loss and/or hunger suppression as well as control over skin or hair pigmentation, hair growth etc. The present invention therefore additionally provides a method of cosmetic treatment of a human or non-human mammalian subject comprising administering to said subject a pre-formulation as described herein. Such a cosmetic method will generally not be a method of therapy (i.e. will not have therapeutic or medical benefit).

One of the advantages of the formulations of the present invention over many other controlled-release compositions is that they are stable to storage in their final form and thus little or no preparation is required at the time of administration. This allows the pre-formulations to be ready-toadminister and also to be supplied in convenient, ready-to-administer form. In a further aspect, the invention therefore provides a pre-filled administration device containing a pre-formulation as described herein. Such a device will generally provide either a single administration or multiple administrations of a composition which will deliver, for example, a dosage of active agent in the range of 1 µg to 5 mg/day.

In a further aspect the invention provides a kit comprising said administration device according to the invention.

The kit can optionally contain instructions for subcutaneous or intramuscular administration of said composition. All compositions described herein are suitable for use in such a kit and may thus be contained therein.

The kits of the invention can optionally include additional administration components such as needles, swabs, and the like and will optionally contain instructions for administration.

BRIEF SUMMARY OF THE ATTACHED FIGURES

FIG. 1a. IVR profile of formulations 911 to 918

FIG. 1b. IVR profile of formulations 1006, 1007, and 1010.

FIG. 2: Peptide Content and Purity (expressed as % of the corresponding values obtained for the reference samples stored at <−15° C.) after storage of formulations G and H for 7 days at 70° C.

FIG. 3. PK-11-413, dose normalized

FIG. 4: PK-11-425, leuprolide plasma concentration versus time over 21 days for formulations 49 and 50.

DETAILED DESCRIPTION OF THE INVENTION

The formulations of the present invention generate a non-lamellar liquid crystalline phase following administration. The use of non-lamellar phase structures (such as liquid crystalline phases) in the delivery of bioactive agents is now relatively well established. A most effective lipid depot system is described in WO2005/117830, and a suitable lipid matrix for use in the present invention is described in that document, the full disclosure of which is hereby incorporated herein by reference. For a description of the most favourable phase structures of such formulations, attention is drawn to the discussion in WO2005/117830 and particularly to page 29 thereof.

All % are specified by weight herein throughout, unless otherwise indicated. Furthermore, the % by weight indicated is the % of the total pre-formulation including all of the components indicated herein. The pre-formulations can optionally consist of essentially only the components indicated herein (including where appropriate additional optional components indicated herein below and in the attached claims) and in one aspect consist entirely of such components.

The lipid-based systems described herein comprise lipid components a) and b), plus organic mono-alcoholic solvent (c), polar solvent (d), peptide active agent (e) and optional antioxidant (f) components.

Preferably the pre-formulation according to the invention has an $L_2$ phase structure. Preferably the pre-formulation forms a non-lamellar (e.g. liquid crystalline) phase following administration.

The present inventors have now surprisingly established that by appropriate choice of types, absolute amounts and ratios of lipid components along with a peptide active agent and at least two solvents including an alcohol and at least one polar solvent, the release properties of the depot compositions formed from the pre-formulations of the invention can be rendered highly advantageous. In particular, by using a mixture of an alcohol and a polar solvent (especially at the ratios close to 1:1 described herein), the advantages of the alcohol solvent on the release profile can be maintained while other properties such as the comfort on administration and/or the viscosity of the formulation can be improved. Alternatively or in addition to this, the release profile of the active agent can be made remarkably level, with the maximum plasma concentration in vivo being only a small multiple of the average or even minimum concentration during the dosing period. Such advantages apply even in comparison with other lipid depot compositions, which in themselves offer previously unobtainable standards in controlled release.

It is important, particularly with certain peptide active agents, such as somatostatin analogues, to control the peak concentration (Cmax) of drug in the plasma to a level equal to or less than that tolerable to the subject, for example to avoid side-effects such as flushing or severe nausea, while providing or achieving a therapeutically effective level over the desired period of release. Generally, the average concentration during the period of release before the next dose is administered, Cave, falls within the therapeutic range. Control over the maximal (Cmax) and minimum (Cmin) concentrations is also important in order to achieve the desired treatment over time. In one embodiment, the initial burst is not the Cmax of the release profile.

Whether or not the initial burst is also the Cmax, preferably the Cmax/Cave ratio is less than 50, preferably less than or equal to 15, more preferably less than or equal to 10, even more preferably less than or equal to 5. Furthermore, it is preferred that the Cave/Cmin ratio is not more than 50, preferably less than or equal to 15, more preferably less than or equal to 10, even more preferably less than or equal to 5. Cmax is defined as is known in the art, as the peak or maximal plasma concentration observed during the period of release before the next dose is administered and Cave is defined as the average plasma concentration during that period of release. Cmin is correspondingly the minimal concentration during that period. Cave can be calculated by calculating the drug present in the plasma as area under the curve (AUC) over the selected period of time, generally the entire period of release before the administration of the next dose, and dividing by that period of time.

Component a)—Diacyl Glycerol

Preferable ranges for component a) are 20-80 wt. %, preferably 30-70 wt. %, more preferably 33-60% (e.g. 43-60%), particularly 38 to 43%. Preferable ranges of component b) are 20-80 wt. %, preferably 30-70 wt. %, more preferably 33-55% (e.g. 35-55%), particularly 38 to 43%.

Ratios of a:b are typically 40:60 to 70:30, preferably 45:55 to 55:45 and more preferably 40:60 to 54:46. Ratios of around 50:50 (e.g. ±2) are highly effective.

Component "a" as indicated herein is preferably at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a). Preferably this component will include at least a portion of C18 lipids (e.g. DAG having one or more C18:0, C18:1, C18:2 or C18:3 non-polar groups), such as glycerol dioleate (GDO) and/or glycerol dilinoleate (GDL). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component b)—Phosphatidyl Choline

Component "b" in the preferred lipid matrices of the present invention is at least one phosphatidyl choline (PC). As with component a), this component comprises a polar head group and at least one non-polar tail group. The difference between components a) and b) lies principally in the polar group. The non-polar portions may thus suitably be derived from the fatty acids or corresponding alcohols considered above for component a. As with component a), the PC will contain two non-polar groups. Again, C18 groups are preferred and may be combined with any other suitable non-polar group, particularly C16 groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

In one embodiment applicable to all aspects of the invention, component b) comprises PC. Preferably the PC is derived from soy. Preferably the PC comprises 18:2 fatty acids as the primary fatty acid component with 16:0 and/or 18:1 as the secondary fatty acid components. These are preferably present in the PC at a ratio of between 1.5:1 and 6:1. PC having approximately 60-65% 18:2, 10 to 20% 16:0, 5-15% 18:1, with the balance predominantly other 16 carbon and 18 carbon fatty acids is preferred and is typical of soy PC.

In an alternative but equally preferred embodiment, the PC component may comprise synthetic dioleoyl PC. This is believed to provide increased stability and so will be particularly preferable for compositions needing to be stable to long term storage, and/or having a long release period in vivo. In this embodiment the PC component preferably contains at least 50% synthetic dioleoyl PC, more preferably at least 75% synthetic dioleoyl PC and most preferably essentially pure synthetic dioleoyl PC. Any remaining PC is preferably soy or egg PC as above.

Since the pre-formulations of the invention are to be administered to a subject for the controlled release of a peptide active agent, it is important that the components are biocompatible. In this regard, the preferred lipid matrices for use in the pre-formulations of the present invention are highly advantageous since both PC and DAGs are well tolerated and are broken down in vivo into components that are naturally present in the mammalian body.

Synthetic or highly purified PCs, such as dioleoyl phosphatidy choline (DOPC) are highly appropriate as all or part of component b). The synthetic dioleoyl PC is most preferably 1,2-dioleoyl-sn-glycero-3-phosphocholine, and other synthetic PC components include DDPC (1,2-Didecanoyl-sn-glycero-3-phosphocholine); DEPC (1,2-Dierucoyl-sn-glycero-3-phosphocholine); DLOPC (1,2-Dilinoleoyl-sn-glycero-3-phosphocholine); DLPC (1,2-Dilauroyl-sn-glycero-3-phosphocholine); DMPC (1,2-Dimyristoyl-sn-glycero-3-phosphocholine); DOPC (1,2-Dioleoyl-sn-glycero-3-phosphocholine); DPPC (1,2-Dipalmitoyl-sn-glycero-3-phosphocholine); DSPC (1,2-Distearoyl-sn-glycero-3-phosphocholine); MPPC (1-Myristoyl-2-palmitoyl-sn-glycero 3-phosphocholine); MSPC (1-Myristoyl-2-stearoyl-sn-glycero-3-phosphocholine); PMPC (1-Palmitoyl-2-myristoyl-sn-glycero-3-phosphocholine); POPC (1-Palmitoyl-2-oleoyl-sn-glycero-3-phosphocholine); PSPC (1-Palmitoyl-2-stearoyl-sn-glycero-3-phosphocholine); SMPC (1-Stearoyl-2-myristoyl-sn-glycero-3-phosphocholine); SOPC (1-Stearoyl-2-oleoyl-sn-glycero-3-phosphocholine); and SPPC (1-Stearoyl-2-palmitoyl-sn-glycero-3-phosphocholine), or any combination thereof.

In some circumstances, such as the absence of preserving agents such as EDTA, the use of synthetic or highly purified PCs (e.g. DOPC) may provide greater stability for the active agent in the formulations. Thus in one embodiment, component b) may comprise (e.g. may comprise at least 75%) synthetic or highly purified (e.g. purity >90%) PCs (e.g. DOPC). This may particularly be in the absence of chelating agents such as EDTA. In an alternative embodiment, component b) may comprise (e.g. comprise at least 75%) naturally derived PCs, such as soy PC or egg PC. This will particularly be where at least one stabilising component (such as an antioxidant, chelator etc) is included in the precursor formulation.

A particularly favoured combination of components a) and b) are GDO with PC, especially GDO with soy PC and/or DOPC. Appropriate amounts of each component suitable for the combination are those amounts indicated herein for the individual components in any combination. This applies also to any combinations of components indicated herein, where context allows.

The ratio of components a:b is in the range 40:60 to 54:46. Preferably the a:b ratio is in the range 45:55 to 54:46, more preferably 47:53 to 53:47. Most preferably the a:b ratio is approximately 50:50.

Component c)—Organic Mono-Alcoholic Solvent

Component c) of the pre-formulations of the invention is an organic mono-alcoholic solvent. Since the pre-formulation is to generate a depot composition following administration (e.g. in vivo), typically upon contact with excess aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Most preferably component c) comprises or consists of ethanol, propanol, ispropanol, or mixtures thereof. Most preferably component c) comprises or consists of ethanol.

In a preferred embodiment, the solvent is such that a relatively small addition to a mixture comprising a) and b) (i.e. preferably below 15%) gives large viscosity reductions, of one order of magnitude or more. As described herein, the addition of 10% organic mono-alcohol solvent can give a reduction of two or more orders of magnitude in viscosity over the solvent-free composition, or over a depot containing only a polar solvent such as water, or glycerol.

The amount of component c) in the pre-formulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 35%, particularly 5 to 25% solvent will provide suitable release and viscosity properties. This will preferably be 5 to 16% (e.g. 6 to 14%) and an amount of around 8% (e.g. 8±2%) is highly effective.

As indicated above, the amount of component c) in the pre-formulations of the invention will be at least sufficient to provide a low viscosity mixture (e.g. a molecular solution, see above) of components a), b), c) and d) and optionally f) and will be easily determined for any particular combination of components by standard methods.

The phase behaviour may be analysed by techniques such as visual observation in combination with polarized light microscopy, X-ray scattering and diffraction techniques, nuclear magnetic resonance, and cryo-transmission electron microscopy (cryo-TEM) to look for solutions, $L_2$ or $L_3$ phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

Typical organic mono-alcoholic solvents suitable for use in the invention include at least one solvent selected from ethanol, propanol, isopropanol, and benzyl alcohol, particularly ethanol.

A highly preferred combination for components a), b) and c) is soy PC, GDO and ethanol. As indicated above, appropriate amounts of each component suitable for the combination are those amounts indicated herein for the individual components, in any combination.

It is preferable that little or none of component c) contains halogen substituted hydrocarbons since these tend to have lower biocompatibility.

Component c) as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c) (single solvent or mixture) should typically be no more than 18 mPas at 20° C. This is preferably no more than 15 mPas, more preferably no more than 10 mPas and most preferably no more than 7 mPas at 20° C.

Component d)—Polar Solvent

Some of the particular benefits of the compositions of the present invention come through the unexpected finding that the use of an alcohol solvent in combination with a polar solvent such as a diol or water allows a significant improvement in the performance of certain lipid-based controlled-release compositions. In particular, the addition of a diol, such as propylene glycol or water has been observed to reduce the viscosity of a lipid/alcohol/active agent formulation without adversely affecting the release profile of the active agent and/or allows the proportion of alcohol to be increased without adversely affecting the release profile and/or allows an improvement in the release profile. By "adversely affecting the release profile" is intended to indicate that the ratio of Cmax/Cave is increased and/or the ratio of Cmax/Cmin is increased (for example increased by a factor of at least 1.2). Similarly an improvement in the release profile indicates that the ratio of Cmax/Cave and/or Cmax/Cmin is decreased (e.g. decreased by a factor of at least 1.2.)

Although it has previously been suggested that lipid controlled-release compositions should be formulated substantially in the absence of water, in order to avoid the conversion to high-viscosity liquid crystalline phases, it has now furthermore been established that a small and carefully controlled amount of a polar solvent such as water can provide considerable benefits. In particular, the inclusion of this polar solvent (preferably comprising water) allows further improvements in controlling the initial release of active agent, allows higher stable loading of some peptide active agents, provides faster depot formation and/or provides further reduced discomfort upon injection. Any one of these factors potentially provides a significant improvement in the context of therapeutic drug delivery, patient health and/or patient compliance.

The pre-formulations of the present invention must thus also contain a polar solvent, component d). A suitable amount will typically be greater than 1% by weight of the pre-formulation, for example 1-30 wt. %, particularly 1.2-20 wt. %, especially 2-18 wt. %. More preferably component d) is present in the range 5-15 wt. %, especially 6-12 wt. %. Component d) is preferably water, propylene glycol or mixtures thereof. In one preferred aspect, the pre-formulations of the invention contain ethanol as component c) with water and/or propylene glycol as component d).

In one embodiment the preformulation comprises at least 1.5% (e.g. at least 4.5%) water as part of component d) (by weight of the total composition) with the remainder being propylene glycol. At least 5% water with the balance of component d) being PG is preferred. Component d) may comprise or consist of water.

In an alternative embodiment, component d) may comprise or consist of propylene glycol.

Preferably the total level of components c) and d) is not more than 35 wt. %, preferably not more than 30 wt. %, preferably 10-30 wt. %, most preferably 12-25%.

The ratio of components c) and d) will also have potential advantages in the compositions of the invention. In particular, by inclusion of some polar solvent which is miscible with the mono-alcohol component (especially water), the slight sensation that may be caused at the injection site from the alcohol content can be substantially eliminated. Thus, in one embodiment, the ratio of components c):d) may be in the range 30:70 to 70:30, more preferably 40:60 to 60:40. In one embodiment, the amount of alcohol component c) by weight is no greater than the amount of polar solvent d). Ratios of c):d) ranging from 30:70 to 50:50 are thus appropriate in such an embodiment. Approximately equal amounts of components c) and d) are highly appropriate.

A highly preferred combination for the lipid matrix aspect is soy PC, GDO, ethanol, and water/propylene glycol or mixtures thereof. As indicated above, appropriate amounts of each component suitable for the combination are those amounts indicated herein for the individual components, in any combination.

Component e)—Peptide Active Agent

The pre-formulations of the present invention contain one or more peptide active agents. Suitable peptide active agents are disclosed and discussed in detail in US WO 2006/075124 and the disclosures of that document are incorporated herein by reference. Suitable peptides for use in the necessary peptides may be naturally occurring or derived from natural peptides, or may be chemically modified or wholly synthetic peptide molecules. Any amino acids may be comprised in the peptides including those described herein, and the peptides may be chemically or enzymatically modified.

Typical peptide actives will be in the range of 500 to 100,000 amu in molecular weight and can evidently include protein active agents. In one embodiment, the polypeptides can have at least one cationic charge at neutral and/or physiological pH, and most preferably will require at least one anionic counter-ion at pH 6.5 or above, preferably at pH 7.5 or above. This counter-ion will be physiologically acceptable, and may thus be a halide or the ion of a physiologically acceptable acid. Acetate counter ions and/or chloride ions are particularly preferred and therefore in one embodiment of the invention, the active agent is a peptide acetate and/or chloride.

Examples of suitable classes of peptides include peptide hormones and synthetic analogues (such as luteinizing-hormone releasing hormone (LHRH) and analogues (eg, leuprorelin, goserelin, buserelin, tryptorelin, degarelix), incretins and incretin mimetics (such as GLP-1 & analogues or glucose-dependent insulinotropic peptide (GIP)), glucagon, insulin and analogues, interferons, vasopressins, calcitonins, etc.), cytokines, antibody fragments (FAbs; scVFs), antimicrobial peptides (g, corticostatins, defensins, histatins), specific targeting peptides (e.g., as the examples described in *Current Opinion Genetics & Development* 10, 71-77 (2006)), venom peptides (e.g., conopeptides), and immunogenic peptides (e.g., fragments of proteins used for vaccination purposes).

In one embodiment, LHRH analogues (also known as GnRH analogues) form a preferred group of active agents for use in the present invention. Preferably such peptides will be structurally related to GnRH I, II and/or III, and/or one or more of the known analogues, including those listed here.

Particularly preferred GnRH analogues are constrained peptides of 6 to 12 alpha-amino acids, of which particular examples include those indicated above, and particularly leuprolide and goserelin, of the sequences indicated above.

In a further embodiment, GLP-1 and its analogues form a further preferred group of active agents. GLP-1 analogues will be peptides, especially of around 30 amino acids, e.g. 20 to 45, especially 25 to 38. Preferably such peptides will be structurally related to GLP-1 and/or one or more of the known analogues, including those listed here. By "GLP-1 analogue", as used herein is indicated any GLP-1 receptor agonist (or less preferably antagonist), including naturally occurring forms of GLP-1, either human or from any other species. These analogues are preferably peptides, peptide derivatives or peptide mimics. Peptide derived GLP-1 agonists are most preferred, especially GLP-1(7-37), GLP-1(7-36)amide, Liraglutide (Novo Nordisk), AVE-010 (ZP10—Zealand Pharma—Sanofi-Aventis), TH0318 (TheraTechnologies), CJC-1131 (ConjuChem), LY548806 (Lilly), Exenatide. (Byetta, Amylin-Lilly) and their derivatives.

In the peptide actives of the present invention, peptides may contain only amino acids selected from those 20 α-amino acids indicated in the genetic code, or more preferably may contain their isomers and other natural and non-natural amino acids, (generally α, β or γ amino acids) and their analogues and derivatives.

Amino acid derivatives are especially useful at the termini of the peptides, where the terminal amino or carboxylate group may be substituted by or with any other functional group such as hydroxy, alkoxy, carboxy (on the N-terminal end), ester, amide, thio, amido, amino (on the C-terminal end), alkyl amino, di- or tri-alkyl amino, alkyl (by which is meant, herein throughout $C_1$-$C_{20}$ alkyl, preferably $C_1$-$C_{18}$ alkyl e.g. methyl, ethyl, n-propyl, isopropyl, n-butyl, iso-, sec- or t-butyl etc.), aryl (e.g phenyl, benzyl, napthyl etc), heteroaryl, or other functional groups, preferably with at least one heteroatom and preferably having no more than 20 atoms in total, more preferably no more than 10 and most preferably not more than 6 atoms (optionally excluding hydrogens).

In one preferred embodiment of the present invention, the peptide active agent will comprise a somatostatin, or any analogue or derivative thereof.

Somatostatin has two active forms produced by alternative cleavage of a single preproprotein: one of 14 amino acids, the other of 28 amino acids. Somatostatin 1-14 is a cyclic peptide hormone having the sequence Ala-Gly-Cys-Lys-Asn-Phe-Phe-Trp-Lys-Thr-Phe-Thr-Ser-Cys (SEQ ID NO: 1), where the two cystine residues are connected by a disulphide bridge to generate a type II β-turn at the key binding sequence of Phe-Trp-Lys-Thr (SEQ ID NO: 2). Somatostatin is a natural peptide hormone also known as Growth Hormone Release Inhibiting Factor and has a role as an antagonist of insulin, glucogen and certain other hormones in the release of somatotrophin (Human Growth Hormone). The biological half-life of natural Somatostatin is very short (1-3 minutes) and so in itself is difficult to formulate as a viable therapeutic. However, the lipid depot compositions of the present invention are highly effective for short-lived active agents and an increasing number of somatostatin analogues are becoming available with higher activities and/or longer clearance times in vivo.

Somatostatin analogues, such as octreotide, lanreotide, vapreotide, pasireotide (SOM 230) and related peptides, are used or indicated in the treatment of a variety of conditions where they are typically administered over an extended period.

Octreotide, for example, is the synthetic octa-peptide with sequence D-Phe-Cys-Phe-D-Trp-Lys-Thr-Cys-Thr-ol (2-7 disulphide bridge) and is typically administered as the acetate salt. Several clinical studies also feature the octreotide pamoate. This derivative retains the key Phe-(D)Trp-Lys-Thr β-turn but, in contrast to the natural hormone, has a terminal half-life of around 1.7 hours. Octreotide is used in treatment of conditions including carcinoid tumours and acromegaly, and after an initial dose is typically given over a sustained period of weeks, or more commonly many months or years. In addition, somatostatin analogues are indicated in the treatment of many cancers since a wide variety of tumours are found to express somatostatin receptors. Of particular interest are those expressing the "sst(2)" and/or "sst(5)" receptor.

The most common "simple" formulation of Octreotide is "Sandostatin"™ from Novartis. This is a solution for subcutaneous (s.c) injection and a 100 μg dose reaches a peak concentration of 5.2 ng/ml at 0.4 hours post injection. The duration of action can be up to 12 hours but s.c. dosing is generally carried out every 8 hours. Evidently, s.c. injection 3 times daily for periods of months or years is not an ideal dosing regime.

In order to avoid the need for multiple daily injections of octreotide, a further formulation is available; "Sandostatin LAR"™, again from Novartis. This is a formulation of octreotide in poly lactic co-glycolic acid microspheres which, after resuspension, may be administered by intra muscular (i.m.) injection.

Carcinoid tumours are intestinal tumour arising from specialised cells with paracrine functions (APUD cells). The primary tumour is commonly in the appendix, where it is clinically benign. Secondary, metastatic, intestinal carcinoid tumours secrete excessive amounts of vasoactive substances, including serotonin, bradykinin, histamine, prostaglandins, and polypeptide hormones. The clinical result is carcinoid syndrome (a syndrome of episodic cutaneous flushing, cyanosis, abdominal cramps, and diarrhea in a patient with valvular heart disease and, less commonly, asthma and arthropathy). These tumours may grow anywhere in the gastrointestinal tract (and in the lungs) with approximately 90% in the appendix. The remainder occurs in the ileum, stomach, colon or rectum. Currently, treatment of carcinoid syndrome starts with i.v. bolus injection followed by i.v. infusion. When sufficient effect on symptoms has been established, treatment with a depot formulation of octreotide formulated in ploy lactic-co-glycolic acid (PLGA) microspheres is started. However, during the first two weeks or more after injection of the depot, daily s.c. injections with octreotide are recommended to compensate for the slow release from the PLGA spheres.

Acromegaly is a rare chronic and insidious hormonal disorder that occurs when the pituitary gland produces excess growth hormone (GH). It most commonly affects middle-aged adults and may lead to premature death.

Diabetes mellitus, hypertension, and increased risk of cardiovascular disease are the most serious health consequences of acromegaly. In addition, patients with acromegaly are at an increased risk of developing colon polyps, which can become cancerous. The prevalence of acromegaly is approximately 60 cases per million population, and the incidence is 3.3 new cases per million per year. The word acromegaly comes from the Greek words for "extremities" (acro) and "great" (megaly), because one of the most common symptoms of this condition is abnormal growth of the hands and feet.

Acromegaly is caused by prolonged overproduction of growth hormone (GH) and excessive production of insulin-like growth factor-I (IGF-I). In 98 percent of cases, the overproduction of GH is caused by a pituitary adenoma. The rate of GH production and the aggressiveness of the tumour vary from patient to patient. Generally, more aggressive tumours are seen in younger patients.

Acromegaly is a severe disease often diagnosed late. Morbidity and mortality rates are high, in particular, because of associated cardiovascular, cerebrovascular, and respiratory disorders and malignancies.

Treatment of acromegaly is initiated by a period of s.c. injections three times per day (optimal daily dose=300 μg octreotide). After the last s.c. dose and providing a suitable effect is observed then treatment with a depot formulation of octreotide formulated in poly lactic-co-glycolic acid (PLGA) microspheres is started. Dose adjustments are made after measurement of biomarkers (HG and IGF-1), typically after around 3 months.

The existing octreotide slow release formulation relies upon a well-established degrading-polymer type of depot formulation. Typically such formulations are based on a biodegradable polymer such poly(lactic acid) (PLA) and/or poly(lactic-co-glycolic acid) (PLGA) and may be in the form of a solution in an organic solvent, a pre-polymer mixed with an initiator, encapsulated polymer particles or (as in the case of octreotide) polymer microspheres.

In one typical embodiment, the peptide active agent (e.g. somatostatin analogue) will generally be formulated as 0.02 to 12% by weight of the total formulation. Typical values will be 0.1 to 10%, preferably 0.2 to 8%, more preferably 0.5 to 6% (e.g. 1 to 3%). These levels may be applied to all aspects of the invention, where context allows. For octreotide, a further preferred range is between 0.5 to 4 wt. %, more preferably 1-3 wt. %, and most preferably 1.5-2.5 wt. %.

In a related embodiment, the peptide active agent may be formulated at a level which cannot easily be achieved in the absence of the polar solvent component of the mixture. In such an embodiment, the peptide active agent (e.g. Somatostatin analogue) content is typically at least 0.7%, preferably at least 1%, more preferably at least 1.8% or at least 2% by weight of formulation. Levels of at least 3% and at least 4% are achievable with the present invention, as are loading levels up to 8, 10 or 12%. Such compositions of the present invention typically not only contain a very high level of peptide active agent (especially Somatostatin analogue, e.g. octreotide), as indicated, but are additionally stable to storage without loss or degradation of the active agent for considerable periods, as indicated herein. Such periods will generally be at least a month at 25° C. or at least a month at 5° C., preferably at least 3 months, and more preferably at least 6 months at 5° C. or alternatively at 25° C. These degrees of stability are applicable to all aspects of the invention, where context allows and relate to stability both of the active agent and of the phase behaviour of the pre-formulation.

In a related embodiment, in the situation where a peptide active agent is highly soluble in the alcohol component, it may be an advantage to limit this solubility of this agent. Without being bound by theory, it is thought that excessive solubility in this alcohol component may result in the alcohol transporting a significant quantity of active agent out of the depot composition as it forms in vivo. Therefore, in one embodiment of the present invention, the polar solvent is used to control the solubility of the active agent in the preformulation so as aid control of the release profile.

In one embodiment, the peptide active agent may be a peptide which is not a somatostatin analogue (as defined herein). For example, the peptide active agent may be a peptide which does not interact as either agonist or antagonist at any of the SST(1) to SST(5) receptors (especially the corresponding human receptors).

In one embodiment, the peptide active agent may be a dual receptor modulator, having a somatostatin analogue directly conjugated to a receptor agonist or antagonist for another receptor. These are referred to herein as "dual receptor agonists. Dual receptor agonists as indicated herein are peptide compounds having at least two distinct domains wherein one domain serves as an agonist for the somatostatin receptor and another serves as an agonist or antagonist for another biological receptor. Such dual agonists are distinct from a single non-specific agonist in that, although the domains may and preferably will be covalently bound together, the domain serving as somatostatin receptor agonist resides on a distinct portion of the peptide sequence from the domain serving to affect the other receptor. That is to say, the dual agonist is a compound in which a peptide sequence having somatostatin receptor function and substantially no function at the second receptor is chemically linked (directly or indirectly) to a sequence having function at the second receptor and substantially no somatostatin receptor agonist function.

In one embodiment, the active agent is not a dual amylin receptor/GLP-1 receptor agonist compound.

In a further aspect, the present invention therefore provides a method for controlling the solubility of a peptide active agent (such as a somatostatin analogue as described herein) in a low viscosity mixture comprising:
a) 20-80 wt. % of at least one diacyl glycerol and/or a tocopherol;
b) 20-80 wt. % of at least one phosphatidyl choline (PC);
c) 5-20 wt. % of at least one biocompatible, organic mono-alcoholic solvent;
e) at least one peptide active agent;
f) optionally at least one antioxidant;
by inclusion of a polar solvent component d) to form a depot precursor formulation. Use of a polar solvent in such a method forms a further aspect.

The pre-formulations and components of the mixture, as well as their performance etc will evidently correspond to those described herein for other aspects.

Similarly, the present invention provides a method for improving the release profile of a peptide active agent (such as a somatostatin analogue as described herein) from a depot composition formed by injection of in a low viscosity mixture comprising:
a) 20-80 wt. % of at least one diacyl glycerol and/or a tocopherol;
b) 20-80 wt. % of at least one phosphatidyl choline (PC);
c) 5-20 wt. % of at least one biocompatible, organic mono-alcoholic solvent;
e) at least one peptide active agent;
f) optionally at least one antioxidant;
by inclusion of a polar solvent component d) in said low-viscosity mixture to form a depot precursor formulation. Use of a polar solvent in such a method forms a further aspect.

The pre-formulations and components of the mixture, as well as their performance etc will evidently correspond to those described herein for other aspects.

Corresponding methods and uses provide for the reduction of injection-site discomfort, reduction of viscosity of the pre-formulation, and/or reduction in initial "burst" release of a low viscosity mixture comprising:
a) 20-80 wt. % of at least one diacyl glycerol and/or a tocopherol;
b) 20-80 wt. % of at least one phosphatidyl choline (PC);
c) 5-20 wt. % of at least one biocompatible, organic mono-alcoholic solvent;
e) at least one peptide active agent;
f) optionally at least one antioxidant;
by inclusion of a polar solvent component d) in said low-viscosity mixture to form a depot precursor formulation. Use of a polar solvent in such a method forms a further aspect.

All of the above uses and methods for improving the various properties of the preformulation and/or the resulting depot composition are preferably applied without negatively affecting the release profile of the peptide active agent.

Where the peptide active agent comprises somatostatin analogue, (e.g. octreotide), suitable doses for inclusion in the formulation, and thus the volume of formulation used, will depend upon the release rate (as controlled, for example by the solvent type and amount used, the antioxidant content and so forth) and release duration, as well as the desired therapeutic level, the activity of the specific agent, and the rate of clearance of the particular active chosen. Typically an amount of around 0.05 to 40 mg per week of depot duration, preferably 0.1 to 20 mg per week duration (e.g. 1 to 10 mg per week) for a duration of 1 to 24 weeks, preferably 2 to 16 (e.g. 3, 4, 8, 10 or 12) weeks. In an alternative embodiment the preformulation may be formulated for dosing weekly (e.g. every 7±1 days). A total dose of 0.05 to 250 mg per dose would be suitable for providing a therapeutic level for between 7 and 168 days. This will preferably be 0.1 to 192 mg, e.g. 0.2 to 160 mg, 0.1 to 1.6 mg, 20 to 160 mg etc. Evidently, the stability of the active and linearity of the release rate will mean that the loading to duration may not be a linear relationship. A depot administered every 30 days might have, for example 0.2 to 20 mg or a 90 day depot have 60 to 120 mg of active agent (e.g. Somatostatin analogue, e.g. octreotide). Evidently also, the biological half-life of the specific active will be particularly important. The half-life of somatostatin, is less than 5 minutes, and so for sustained release, a relatively large amount (e.g. towards the higher end of the range) will be needed. For an analogue such as octreotide, with a much longer half-life, the amount needed will evidently be lower. Appropriate levels for other actives will be established easily by those of skill in the art by reference to the known therapeutic level, the desired duration of action and the volume which is to be injected. A good base calculation would be to multiply a typical daily dose of the active agent by the number of day's duration of the depot. The formulation can then be tested for linearity of release and adjusted as appropriate.

It is a remarkable development of the present formulations that very short half-life peptide active agents, comprising, e.g. somatostatin and its analogues can be prepared and administered in a depot precursor of the present invention, and will provide controlled release over several days or even weeks. This is in spite of the remarkably short biological half-life of the active agent (e.g. less than 1 hour, preferably less than 15 minutes, e.g. less than 5 minutes). Thus, in one embodiment, the active agent has a half-life of less than 1 hour, e.g. less than 15 minutes and the preformulation forms a depot which provides sustained release for at least 7 days, preferably at least 14 days, more preferably at least 28 days.

Like essentially all organic molecules, lipids and biologically active agents are thermodynamically unstable to oxidation. As a result, many lipid formulations, including those comprising bioactive agents such as APIs are susceptible to degradation upon storage, especially by oxidation.

In a highly preferred embodiment, the lipid matrix aspect is soy PC, GDO, ethanol, and water/propylene glycol or mixtures thereof, and the peptide active agent comprises somatostatin or a somatostatin analogue. As indicated above, appropriate amounts of each component suitable for the combination are those amounts indicated herein for the individual components, in any combination.

Optional Component f)—Antioxidant

Component f) is an antioxidant. Most preferably it is selected from ascorbic acid, ethylenediaminetetraacetic acid (EDTA) and citric acid.

In all aspects of the invention, component f) is typically present at a weight ratio of antioxidant to peptide active agent of 1:50 to 1:1500, preferably 1:100 to 1:1300, and most preferably 1:150 to 1:1250. Since typical antioxidants are of lower molecular weight that the peptide active agents, the proportion by weight of antioxidant may be relatively small. For example, with a small molecular weight pH adjuster (e.g. less than 500 amu), 0.0001 to 0.5% of the composition may be antioxidant, preferably 0.0005 to 0.2%, more preferably 0.0008 to 0.1%, e.g. 0.001 to 0.015%.

Unfortunately, many common antioxidants are not highly compatible with lipid systems. Indeed, the present inventors have previously established that some antioxidants commonly used in previous systems can cause increased degradation of active agents in a lipid system. This applies particularly to peptide active agents. The present inventors have therefore analysed a variety of potential antioxidant compounds and classes for use with lipid based matrix systems and have surprisingly found that one particular class of antioxidants is unusually well suited for use in these systems.

The antioxidant component is generally included in the range 0.0001 to 0.5% by weight of the total pre-formulation. Around 0.0005 to 0.015% of antioxidant (particularly EDTA) is particularly preferred, especially in combination with the other preferred components and ranges indicated herein above and below.

Stability data using a number of different antioxidants demonstrate that EDTA antioxidants are surprisingly more efficient than other antioxidants in suppressing the oxidative degradation of bioactive agents. EDTA as antioxidant can also show a synergistic effect in combination with the antioxidants of the present invention, in maintaining the chemical and physical stability of the peptide active agent and complete pre-formulation. EDTA has a stabilising effect on the active agent.

By "stabilising" is indicated an increase in solubility or dispensability of a component (especially an active agent) in the depot delivery system, or alternatively an increase in the stability of the composition, especially with regard to the physical and chemical stability of the dissolved or dispersed active agent. An increase in stability may thus be demonstrated by dissolution, dispersion or suspension of a greater amount of active agent in the presence of the antioxidant than would be achieved by equilibration, such as by agitation for a prolonged period (e.g. 5 days at 25° C.), in the absence of antioxidant. Equally, an increase in stability may be demonstrated by the chemical and/or physical stability of a peptide active agent in a lipid formulation for a greater period than would be observed in the absence of an antioxidant. This would preferably be tested under conditions of typical storage, such as 0-5° C., 25° C. and/or ambient temperature. This is further described herein below.

Optional Additional Components

In one particularly preferred embodiment of the present invention, the compositions (preformulations and resulting depots) do not include fragmentation agents, such as polyethyleneoxide or poly(ethylene glycol) (PEG) fragmentation agent, e.g. a PEG grafted lipid and/or surfactant.

For example, the compositions preferably do not include fragmentation agents such as Polysorbate 80 (P80), or other Polysorbates (e.g. Polysorbate 20), PEGylated phospholipids (PEG-lipids such as DSPE-PEG(2000), DSPE-PEG (5000), DOPE-PEG(2000) and DOPE-PEG(5000)), Solutol HS 15, PEGylated fatty acids (e.g. PEG-oleate), block co-polymers such as Pluronic® F127 and Pluronic® F68, ethoxylated castor oil derivatives (e.g. Chremophores), PEGylated glyceryl fatty acid esters (such as TMGO-15 from Nikko Chemicals) and PEGylated tocopherols (such as d-alpha tocopheryl poly(ethylene glycol)1000 succinate known as Vitamin E TPGS from Eastman.

However, the polypeptide active as a powder (e.g. in the kit of the invention), as well as active agent dissolved in the lipid formulation, may gain stability (both storage and in vivo stability) by certain stabilising additives. Such additives include sugars (e.g. sucrose, trehalose, lactose etc.), polymers (e.g. polyols such as carboxy methyl cellulose), amino acids (such as methionine, glutamate, lysine etc.), lipid-soluble acid components such as HCl, anionic lipids and/or surface active agents (such as dioleoyl phosphatidyl glycerol (DOPG), palmitoyloleoyl phosphatidylglycerol (POPG) and oleic acid (OA)).

Single-dose formats must remain stable and potent in storage prior to use, but are disposable after the single use. In one embodiment, a single dose format is stable at refrigerated conditions (e.g. 0-5° C.) for at least 12 months. Furthermore such a preformulation may be stable at room temperature (e.g. 25° C.) for at least 12 months. Multi-dose formats must not only remain stable and potent in storage prior to use, but must also remain stable, potent and relatively free of bacteria over the multiple-dose use regimen administration period after the first use in which a seal has been compromised. For this reason multi-dose formats often require a anti-microbial or microbial-static agent, e.g. bacteriostatic agent, preservative.

However, the production of preserved pharmaceutical preparations containing protein or peptide actives has often proven difficult, as when preservatives are used, these give rise to stability problems. Often the proteins are inactivated and aggregates are formed, which may sometimes lead to reported injection site intolerance or immunogenicity to the active. This can be further aggravated by additional excipients or formulation components.

In one aspect each of the embodiments herein can optionally contain an antimicrobial or microbial-static agent, which includes bacteriostatic agents and preservative. Such agents include benzalkonium chloride, m-cresol, benzyl alcohol or other phenolic preservatives. Typical concentrations as known in the art can be used.

However, surprisingly it has been found that the present formulations with a peptide active agent do not require an additional preservative, anti-microbial or microbial-static agent, e.g. bacteriostatic or bacteriocide or additional amount of such agent to provide a multi-use format. The formulations as described herein provide a preservative effect with an acceptable peptide stability and formulation stability. They can be used for single-dose as well as for multiple-dose use. In this regard, preferred formulations herein for multi-use format can contain ethanol, propylene glycol, citric acid and/or EDTA as described, preferably in sufficient concentrations to not only provide their primary benefit as taught herein but also at sufficient concentration, either alone or in any combination, to provide the preservative effect while maintaining stability of the active and the formulation.

Additional components above those mentioned as components a) to f) will, where present at all, preferably be present in an amount of 0 to 5% (e.g. 0.01% to 5%) by weight, preferably no more than 2% by weight and more preferably no more than 1% by weight.

In one embodiment, components a) and b) (allowing for any impurity inherent in the nature of these components) make up at least 95% of the lipid components of the composition. Preferably at least 99% of the total lipid content of the pre-formulation consists of components a) and b). Preferably the lipid component of the pre-formulation consists essentially of components a) and b).

Administration

The pre-formulations of the present invention are generally formulated to be administered parenterally. This administration will generally not be an intra-vascular method but will preferably be subcutaneous (s.c.), intracavitary or intramuscular (i.m.). Typically the administration will be by injection, which term is used herein to indicate any method in which the formulation is passed through the skin, such as by needle, catheter or needle-less (needle-free) injector. It is, however, possible to take advantage of the high loading and other beneficial characteristics of the present formulation in non-parenteral applications, including topical or systemic application to skin, mucous membranes, nasal, buccal and/or oral cavities. Preferably, such non-parenteral administration is for topical use.

Preferred parenteral administration is by i.m or s.c. injection, most preferably by deep s.c. injection. An important feature of the composition of the invention is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

The preferred lipid pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of components a:b are in the region of 40:60 to 70:30, preferably 45:55 to 55:45 and more preferably 40:60 to 54:46. Ratios of around 50:50 (e.g. ±2) are highly preferred, most preferably around 50:50.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or similar injecting dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 5 wt %, preferably greater than 7%, and most preferably greater than 9% of organic mono-alcoholic solvent (component c) having a viscosity reducing effect. The preformulations of the invention which are in $L_2$ phase form one preferred set of preformulations and these will generally contain at least 2% water as polar solvent.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 µm syringe filter. A typical range of suitable viscosities would be, for example, 0.1 to 5000 mPas, preferably 1 to 1000 mPas, more preferably 10 to 750 mPas and most preferably 25 to 500 mPas at 20° C.

It has been observed that by the addition of small amounts of low viscosity organic mono-alcoholic solvent, as indicated herein, a very significant change in viscosity can be provided. For example, the addition of only 5% solvent to a lipid mixture can reduce viscosity 100-fold and addition of 10% may reduce the viscosity up to 10,000 fold. In order to achieve this non-linear, synergistic effect in lowering viscosity it is important that a solvent of appropriately low viscosity and suitable polarity be employed. Such solvents include those described herein infra. Preferred low-viscosity mixtures include molecular solutions, including dispersions of the peptide active agent in a molecular solution of the other components.

Upon administration, the preferred lipid-based pre-formulations of the present invention undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as normal or reversed hexagonal or cubic liquid crystalline phases or mixtures thereof. Further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure to excess aqueous fluid, the pre-formulations of the invention lose some or all of the organic solvent included therein (e.g. by diffusion) and take in aqueous fluid from the bodily environment (e.g. the in vivo environment). For lipid pre-formulations, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

By incorporation of at least 10% of a polar solvent (especially at least 5% water) into the pre-formulations, it is believed that the rate of phase transition to a non-lamellar (e.g. liquid crystalline) phase at the surface of the injected pre-formulation can be enhanced in comparison with compositions containing organic solvents in the substantial absence of water. The performance of the resulting depot is thus improved and further control over the release of active agent achieved.

The depot systems formed by the formulations of the present invention are highly effective in protecting the active agent from degradation and thus allow an extended release period. The formulations of the invention thus may provide in vivo depots of peptide active agents which require administration only once every 5 to 90 days preferably 5 to 60 days, more preferably 6 to 32. Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally ±1 day) or monthly (e.g. every 28 or 30 days (optionally ±7 days) administration so that the need to administer is not forgotten.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of peptide active agent (e.g. Somatostatin analogue, e.g. octreotide) to be selected by reference to the species, age, sex, weight, and/or physical condition of the individual subject, by means of injecting a selected volume.

The present invention thus provides for methods comprising the selection of a dosing amount specific to an individual, particularly by subject weight. The means for this dose selection is the choice of administration volume.

In one preferred aspect, the present invention provides a pre-formulation comprising components a), b), c), d), f) and at least one peptide active agent (e.g. somatostatin analogue, e.g. octreotide) as indicated herein. The amounts of these components will typically be in the range 30-70% a), 30-60% b), 5-20% c) and 0.1-20% d), with the peptide active agent (e.g. somatostatin analogue, e.g. octreotide) present at 0.01% to 10%, (such as 36-44% a), 36-44% b), 3-18% c) and 5-18% d) (preferably including at least 2% water), with the peptide active agent (e.g. somatostatin analogue, e.g. octreotide) present at 1% to 3%), wherein the ratio of a:b is in the range 40:60 to 54:46.

Typically, component f) is present at an antioxidant to peptide active agent molar ratio of 1:50 to 1:1500, preferably 1:100 to 1:1300, and most preferably 1:150 to 1:1250. Since typical antioxidants are of lower molecular weight than peptide active agent (e.g. somatostatin analogue, e.g. octreotide), the proportion by weight of antioxidant may be relatively small. For example, with a small molecular weight pH adjuster (e.g. less than 500 amu), 0.001 to 5% of the composition may be antioxidant, preferably 0.002 to 2%, more preferably 0.002 to 0.15%, e.g. 0.002 to 0.015%.

The pre-formulations of the present invention are highly advantageous in that they are stable to prolonged storage in their final "administration ready" form. As a result, they may readily be supplied for administration either by health professionals or by patients or their carers, who need not be fully trained health professionals and may not have the experience or skills to make up complex preparations. This is particularly important in long-duration, slow-effecting diseases such as diabetes.

Devices

In a yet further aspect, the present invention provides a disposable administration device (which is also to include a device component) pre-loaded with a measured dose of a pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

The pre-filled devices of the invention may also suitably be included in an administration kit, which kit also forms a further aspect of the invention. In a still further aspect, the invention thus provides a kit for the administration of at least one peptide active agent, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

Kits

The invention provides for a pre-filled administration device as indicated herein and a kit as indicated herein comprising a pre-formulation as described herein.

In an alternative aspect of the present invention, the "kit" may contain at least two vessels, a first containing a low viscosity mixture of components a) to d), as described here, and a second containing a measured dose of at least one peptide active agent as described herein. The antioxidant component f) may be formulated with the active agent, or more preferably as part of the low viscosity mixture, which will then comprise components a) to d) and f).

Such a "two component kit" may comprise the peptide active agent as a powder formulation in one vial or pre-filled syringe and components a) to d) (and optionally f)) in a second vial or pre-filled syringe. In the case of two syringes, before injection, the pre-filled syringes are connected and the powder comprising active agent is mixed with the matrix formulation by moving the syringe barrels back and forth, forming a solution or suspension which is injected. Alternatively, the liquid lipid formulation is drawn from one vial, or is pre-filled into a syringe, and is injected into a vial containing peptide powder. This formulation may subsequently be mixed by hand shaking or other suitable reconstitution method (e.g. vortex mixing etc.). The solvent component may be present in either or both vessels (e.g. vials or syringes). Where the solvent is at least partially constituted with the active agent, this will generally be in the form of a solution or suspension.

In this aspect, the invention therefore provides a two component kit comprising
i) a first vessel containing a low viscosity mixture of components a) to d) as described herein;
ii) a second vessel containing at least one peptide active agent,
iii) an antioxidant component f) optionally in a third vessel, preferably in the second vessel, or most preferably in the first vessel;
iv) optionally and preferably at least one of:
  1) at least one syringe (which may be one or both of said first and second vessels);
  2) a needle for administration, such as those described herein;
  3) instructions for generation of a composition of the invention from the contents of the first and second vessels;
  4) instructions for administration, whereby to form a depot as described herein.

Preferred Features and Combinations

In combination with the features and preferred features indicated herein, the pre-formulations of the invention may have one or more of the following preferred features independently or in combination:

All proportions indicated herein may optionally be varied by up to 10% of the amount specified, optionally and preferably by up to 5%;

Component a) comprises, consists essentially of or preferably consists of GDO;

Component b) comprises, consists essentially of or preferably consists of soy PC;

Component c) comprises, consists essentially of or preferably consists of a 1, 2, 3 or 4 carbon alcohol, preferably isopropanol or more preferably ethanol;

Component d) comprises, consists essentially of or preferably consists of a polar solvent such as water, propylene glycol, or mixtures thereof;

Component f) comprises, consists essentially of or preferably consists of ascorbic acid, ethylenediaminetetraacetic acid (EDTA), and/or citric acid;

The pre-formulation contains at least one peptide active agent, preferably a Somatostatin analogue such as Octreotide;

The pre-formulation contains at least one somatostatin analogue (as described herein) such as at least one peptide which has agonistic and/or antagonistic effect at at least one of the SST(1)-SST(5) receptors (e.g. in humans).

The pre-formulation does not contain any somatostatin analogue (as described herein);

The pre-formulation has a low viscosity as indicated herein.

The pre-formulation comprises forms a liquid crystalline phase as indicated herein upon in vivo administration.

The pre-formulation generates a depot following in vivo administration, which depot releases at least one active agent at a therapeutic level over a period of at least 7 days, preferably at least 21 days, more preferably at least 28 days.

The pre-formulation has a higher loading of peptide active agent (e.g. Somatostatin analogue, e.g. octreotide) than is stable in the same formulation in the absence of component e).

The pre-formulation has a higher loading of peptide active agent (e.g. Somatostatin analogue, e.g. octreotide) than is obtainable by equilibration at 25° C. of the same formulation in the absence of component f).

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 5 to 90 days, preferably 6 to 32 days (for example 7 days or 28-31 days).

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration once every 5 to 90 days, preferably 5 to 60 days, more preferably 6 to 32 days.

In combination with the features and preferred features indicated herein, the pre-filled devices of the invention may have one or more of the following preferred features independently or in combination:

They contain a preferred formulation as indicated herein;

They comprise a needle smaller than 20 gauge, preferably no larger than 23 gauge;

They contain a single dose of 1 to 2000 mg of peptide active agent (e.g. Somatostatin analogue, e.g. octreotide), preferably 0.1 to 100 mg and more preferably 1-50 mg, most preferably 5-35 mg They contain peptide active agent Somatostatin analogue (e.g. octreotide or exenatide) at around 1 to 100 mg.

They contain a homogeneous mixture of a composition of the invention in ready-to-inject form.

They contain a formulation of components a) to c) for combination with a peptide active agent whereby to form a preformulation of the invention.

They contain a peptide active agent for combination with a formulation of components a) to c) and optionally e), whereby to form a preformulation of the invention.

They contain a total volume for administration of no more than 5 ml, preferably no more than 3 ml more preferably no more than 1.5 ml.

In combination with the features and preferred features indicated herein, the kits of the invention may have one or more of the following preferred features independently or in combination:

They contain a preferred formulation as indicated herein;
They contain a pre-filled device as indicated herein;
They contain a needle smaller than 20 gauge, preferably no larger than 23 gauge;
They contain a single dose of 1 to 200 mg of peptide active agent (e.g. Somatostatin analogue, e.g. octreotide), preferably 1 to 100 mg and more preferably 1-50 mg;
They contain peptide active agent. Somatostatin analogue, e.g. octreotide, at around 1 to 100 mg;
They contain a "two compartment kit" comprising at least two vessels containing a lipid formulation of the invention and a peptide active agent (e.g. Somatostatin analogue, e.g. octreotide) powder, respectively.
They contain a total volume for administration of no more than 5 ml, preferably no more than 3 ml more preferably no more than 1.5 ml.
They contain instructions for administration by a route and/or at a frequency as indicated herein;
They contain instructions for administration for use in a method of treatment as described herein.

The Invention will now be further illustrated by reference to the following non-limiting Examples and the attached Figures.

EXAMPLES

Abbreviations

OCT(Cl) Octreotide hydrochloride (PolyPeptide Labs., USA)
SOM(Ac) Somatostatin 1-14 acetate (PolyPeptide Labs., USA)
LEU(Ac) Leuprolide acetate (PolyPeptide Labs., USA)
TTA Triptorelin acetate (Bachem, Switzerland)
TTP Triptorelin pamoate (Bachem, Switzerland)
SPC Soy phosphatidylcholine (Lipoid, Germany)
GDO Glycerol dioleate (Danisco, Denmark)
DOPC Dioleoyl phosphatidylcholine (NOF, Japan)
EtOH Ethanol (99.5 vol %, Ph. Eur., USP)
PG Propylene glycol (Ph. Eur., USP)

Example 1

Manufacturing of OCT-Containing Products

TABLE 1

Composition of OCT-containing products.

| Formulation | Ingredient | OCT (Cl) | SPC | GDO | EtOH | PG | EDTA-water[1] |
|---|---|---|---|---|---|---|---|
| A | (wt %) | 2.44 | 43.78 | 43.78 | 5.00 | 5.00 | — |
| B | (wt %) | 2.44 | 42.28 | 42.28 | 6.50 | 6.50 | — |
| C | (wt %) | 2.44 | 45.53 | 45.53 | 6.50 | — | — |
| D | (wt %) | 2.44 | 38.78 | 38.78 | 10.00 | — | 10.00 |
| E | (wt %) | 2.44 | 33.78 | 33.78 | 15.00 | — | 15.00 |

[1]The concentration in the solution is 0.10 mg EDTA/mL; this solution was prepared by mixing 10 mg EDTANa$_2$ in water.

Depot precursors with the compositions presented in Table 1 were manufactured by first preparing a peptide stock, by weighing the ingredients as described in Table 2 and mixing on a shaking table (250-300 rpm) to homogeneous solutions.

TABLE 2

Preparation of peptide stock solutions.

| Formulation | Ingredient | OCT(Cl) | EtOH | PG | EDTA-water |
|---|---|---|---|---|---|
| A | (g) | 2.44 | 5.00 | 5.00 | — |
| B | (g) | 2.44 | 6.50 | 6.50 | — |
| C | (g) | 2.44 | 6.50 | — | — |
| D | (g) | 2.56 | — | — | 10.50 |
| E | (g) | 0.28 | — | — | 1.73 |

For manufacturing of A, B and C, the following amounts (Table 3) of SPC and GDO were weighted directly into the recipient containing the OCT(Cl) stock solution.

TABLE 3

Amounts of SPC and GDO added for preparation of CAM2029-BP, -BR, and -BU.

| Formulation | Ingredient | SPC | GDO |
|---|---|---|---|
| A | (g) | 43.78 | 43.78 |
| B | (g) | 42.28 | 42.28 |
| C | (g) | 45.53 | 45.53 |

The mixtures were then placed on a shaking table (250-300 rpm) until homogeneous solutions were obtained.

For manufacturing of formulation D, a lipid stock was prepared by mixing (shaking table (250-300 rpm)) 88.58 g SPC, 22.84 g EtOH and 88.58 g GDO to a homogeneous solution. The final formulation was then obtained by combining 87.56 g lipid stock and 12.44 g peptide stock solution and mixing (shaking table (250-300 rpm)) to homogeneous.

For manufacturing of formulation E, a lipid stock was prepared by mixing (shaking table (250-300 rpm)) 4.09 g SPC, 1.82 g EtOH and 4.09 g GDO to a homogeneous solution. The final formulation was then obtained by combining 8.26 g lipid stock and 1.74 g peptide stock solution and mixing (shaking table (250-300 rpm)) to homogeneous.

Example 2

In-Vitro Release from OCT-Containing Products

Formulations with the composition presented in Table 4 were manufactured by first preparing the corresponding OCT(Cl) stock solutions in EtOH, EtOH:PG mixture or respectively water (as described in Example 1 above), followed by mixing with the other components until homogeneous solutions were obtained.

TABLE 4

Composition of OCT-containing products evaluated in the accelerated in vitro release (IVR) experiment.

| Formulation | Ingredient | OCT (Cl) | SPC | GDO | EtOH | PG | Water |
|---|---|---|---|---|---|---|---|
| 911 | (wt %) | 2.43 | 43.72 | 43.79 | 5.02 | 5.04 | |
| 912 | (wt %) | 2.43 | 42.08 | 42.13 | 6.56 | 6.81 | |
| 913 | (wt %) | 2.43 | 41.26 | 41.23 | 7.51 | 7.58 | |
| 914 | (wt %) | 2.43 | 45.41 | 45.60 | 6.56 | | |
| 916 | (wt %) | 2.43 | 33.70 | 33.73 | 15.09 | | 15.06 |
| 917 | (wt %) | 2.44 | 38.70 | 38.68 | 10.04 | | 10.14 |
| 918 | (wt %) | 3.64 | 33.08 | 33.07 | 15.08 | | 15.13 |
| 1006 | (wt %) | 2.00 | 41.48 | 41.48 | 7.55 | | 7.49 |
| 1007 | (wt %) | 2.00 | 36.49 | 36.49 | 12.50 | | 12.53 |
| 1010 | (wt %) | 2.00 | 38.96 | 38.95 | 10.12 | | 9.97 |

Evaluation of accelerated IVR of OCT from each of the formulations presented above was carried out by injecting approximately 100 mg (±20%) into a glass vial containing 5 mL of phosphate buffered saline:acetonitrile 85:15 (v/v) mixture. The vials were sealed, and incubated at room temperature for up to 48 h. Sampling was carried out at different time points from the initiation of the experiment, by slowly pulling out 0.2 mL of the aqueous phase, which was collected directly into a 0.3 mL HPLC polypropylene vial. The analysis was performed by HPLC-UV using an analytical column (ACE-5 C18, 50×3.0 mm) with gradient elution (mobile phase A: 0.1 vol. % trifluoroacetic acid (TFA) in water; mobile phase B: 0.1 vol. % in 95 vol. % methanol, 5 vol. % water) and UV detection at 282 nm.

The results obtained are presented in FIG. 1 (a and b)

Example 3

Stability of OCT-Containing Products with Vs. without EDTA

A formulation (batch size 110 g) with the composition OCT(Cl)/SPC/GDO/EtOH 3.74/43.13/43.13/10.00 (all in wt %) was manufactured by first dissolving 4.114 g OCT(Cl) in 11.000 g EtOH, followed by sequential addition of 47.433 g SPC and 47.433 g GDO, and mixing to a homogeneous solution (91).

One sample (G) containing 3.37 wt % OCT(Cl) (approximately 2.98 wt % OCT base) by mixing 0.9 g formulation 91 with 0.1 mg of a solution containing 0.1 wt % of EDTA in HPLC-grade water.

One sample (H) containing 3.37 wt % OCT(Cl) was prepared by mixing 0.9 g formulation 91 with 0.1 mg HPLC-grade water.

The samples were divided each into two aliquots of about 0.4 g/vial; one aliquot/sample was incubated at 70° C., whereas the other was placed at <−15° C. (reference). All samples were analysed after 7 days of incubation in the above-mentioned conditions by using a normal-phase HPLC (analytical column LiChrospher Diol 5 µm, 250×3.2 mm) UV/DAD-based analytical method for quantification of OCT and relative determination of OCT-related substances. The presence of EDTA in the water phase considerably improved the stability of OCT in the lipid matrix, as shown in the results presented in FIG. 2.

Example 4

Injectability of OCT-Containing Products

The injectability is here defined as the flow rate of the evaluated fluid from a syringe (specified by its volume and design) through a needle (specified by its needle gauge and length) subjected to a constant force against atmospheric pressure.

For filling purposes, a thick needle was preferred, e.g. an 18G needle. When the syringe was filled with the necessary amount of formulation, the thick needle was exchanged for the needle to be examined. By pressing on the plunger with the new needle in place, the entrapped air was removed. The excess formulation was wiped off with a paper tissue and the starting weight (grams) of the filled syringe was measured. The syringe was then mounted in a vertical position using a metallic stand with holder and with the needle facing down. The ejected fluid was collected directly in a glass vial.

A 20N weight was placed centered on the plunger and the timer was started when the weight and the plunger come into contact. The time to empty the syringe (seconds) was then monitored. After the syringe has been emptied, its final weight (grams) was measured. At least two repeat measurements for each sample and type of needle were performed.

The injectability was calculated by use of the following equation:

$$\text{Injectability} = \frac{(\text{Starting weight} - \text{Final weight})}{\text{Injection time}} (\text{mg/s})$$

The injectability of several OCT-containing products is presented in Table 5.

TABLE 5

Injectability (mg formulation/s) of OCT-containing products through 23 G thin-wall (Terumo Neolus NN-2316R), respective 25 G thin-wall (Terumo Neolus NN-2516R) 16 mm-long needles. The syringes used were BD 1 mL plast Luer-Lock (#309628).

| Formulation | Injectability (mg/s) through 23 G needle | Injectability (mg/s) through 25 G needle |
|---|---|---|
| 91 | 71 | 25 |
| 911 | 49 | 17 |
| 912 | 86 | 38 |
| 913 | 126 | 49 |
| 914 | 32 | 12 |
| 916 | 252 | 109 |
| 917 | 126 | 49 |
| 918 | 308 | 115 |

Example 5

In Vivo PK Studies in Rats

Animals and Source

Male SPF Sprague-Dawley rats (NTAC:SD) from M&B Taconic Europe A/S (Ejby, Denmark) were used in the studies. At arrival the rats were 8 to 9 weeks old, with a bodyweight in the range from 275 to 300 g. An acclimatization period of at least 5 days was allowed before dosing.

Housing

The rats will be kept in pairs in transparent polycarbonate cages (Macrolon® type III; Scanbur BK A/S, Karlslunde, Denmark) with a floor area of 810 $cm^2$. Aspen wooden chopping (Tapvei Aspen Bedding, Tapvei Oy, Kortteinen, Finland) were used for bedding material. Wood wool for nest building (PM 90 L "Bobyggnadsmaterial", Tapvei) and a piece of wood ("Gnagpinne medium", Tapvei) were used as environmental enrichment. Complete pelleted rodent diet (Labfor R70, Kimstad, Sweden) and water were available ad libitum.

Dosing

The animals were dosed according to Camurus internal standard operating procedure (SOP PK12-3). In brief, dosing was performed by subcutaneous injections between the scapulae under light isofluran anesthesia, using a 1-mL Luer-lock syringe and a 25-mm 23G needle.

Blood Sampling

Blood samples were collected from awake animals by sub-lingual bleeding. Sampling time points was pre-dose, and 1 hour, 6 hours, 1 day, 2 days, 5 days, 8 days, 14 days, 21 days, 28 days and 35 days after dosing. Blood was collected into EDTA-treated test tubes (Capiject 3T-MQK, Terumo Medical Corporation), placed on ice immediately after collection. After centrifugation (approximately 1500× g, at 5° C. for 10 min) the plasma was transferred new test tubes and stored below −70° C. until analysis.

Bioanalysis

Analysis of OCT—The plasma samples was analysed with the ELISA kit S-1275 (Bachem/Peninsula Laboratories) "Octreotide—EIA Kit, Host: Rabbit, High Sensitivity", adapted for analysis of OCT in rat EDTA plasma.

Results

Pharmacokinetic (PK) profiles for formulations 91, 911 and 912 are shown in FIG. 3.

Example 6

Manufacturing of Formulations Containing Leuprolide Acetate (Leuprorelin—LEU(Ac))

Leuprolide compositions according to the invention were prepared with the compositions as indicated in Table 6. The formulations were prepared by first dissolving the LEU(Ac) in the EtOH, WFI and/or PG components, whereafter the lipid components were added sequentially, starting with SPC and followed by GDO. The final formulations were mixed on a shaking table at 250-300 rpm until clear and homogenous liquid solutions were obtained. The formulations were finally subjected to sterile filtration (0.2 μm sterile PVDF filter from Millipore) under 2 bar nitrogen pressure.

TABLE 6

Composition (wt %) of leuprolide acetate (LEU(Ac)) formulations.

| Formulation# | LEU(Ac) | SPC | DOPC | GDO | EtOH | WFI | PG |
|---|---|---|---|---|---|---|---|
| 49 | 2.70[1] | 43.65 | — | 43.65 | 10.00 | — | — |
| 50 | 2.70[1] | 37.65 | — | 37.65 | 12.00 | 10.00 | — |
| 51 | 1.62[2] | 38.19 | — | 38.19 | 12.00 | 10.00 | — |
| 52 | 2.70[1] | 33.65 | — | 33.65 | 15.00 | 15.00 | — |
| 53 | 2.70[1] | 42.15 | — | 42.15 | 6.50 | — | 6.50 |
| 54 | 2.70[1] | 41.15 | — | 41.15 | 7.50 | — | 7.50 |
| 55 | 2.70[1] | 38.65 | — | 38.65 | 10.00 | — | 10.00 |
| 56 | 1.62[2] | 41.69 | — | 41.69 | 7.50 | — | 7.50 |
| 57 | 2.70[1] | — | 41.15 | 41.15 | 7.50 | — | 7.50 |

[1]Corresponding to 25 mg leuprolide acetate per mL when corrected for peptide purity and content and formulation density.
[2]Corresponding to 15 mg leuprolide acetate per mL when corrected for peptide purity and content and formulation density.

Example 7

Manufacturing of Formulations Containing Triptorelin Acetate (TTA) and Triptorelin Pamoate (TTP)

Triptorelin acetate and pamoate compositions according to the invention were prepared with the compositions as indicated in Table 7. The formulations were prepared by first mixing the TTA or TTP in the EtOH and PG components, whereafter the lipid components were added sequentially, starting with SPC and followed by GDO. The final formulations were mixed on a shaking table at 250-300 rpm until clear and homogenous liquid solutions were obtained. The formulations were finally subjected to sterile filtration (0.2 μm sterile PVDF filter from Millipore) under 2 bar nitrogen pressure.

TABLE 7

Composition (wt %) of triptorelin acetate (TTA) and triptorelin pamoate (TTP) formulations.

| Formulation# | TTA | TTP | SPC | GDO | EtOH | PG |
|---|---|---|---|---|---|---|
| 58 | 3.00[1] | — | 41.00 | 41.00 | 7.50 | 7.50 |
| 59 | 3.00[1] | — | 38.50 | 38.50 | 10.00 | 10.00 |
| 60 | — | 3.50[1] | 40.75 | 40.75 | 7.50 | 7.50 |
| 61 | — | 3.50[1] | 38.25 | 38.25 | 10.00 | 10.00 |

[1]Corresponding to 25 mg triptorelin free base per mL when corrected for peptide purity and content and formulation density.

Example 8

Manufacturing of Further Formulations Containing Octreotide Chloride (OCT(Cl))

Octreotide compositions according to the invention were prepared with the compositions as indicated in Table 8. The formulations were prepared by first dissolving the OCT(Cl) in the EtOH, WFI and/or PG components, whereafter the lipid components were added sequentially, starting with SPC and followed by GDO. The final formulations were mixed on a shaking table at 250-300 rpm until clear and homogenous liquid solutions were obtained. The formulations were finally subjected to sterile filtration (0.2 μm sterile PVDF filter from Millipore) under 2 bar nitrogen pressure.

TABLE 8

Composition (wt %) of octreotide chloride (OCT(Cl)) formulations.

| Formulation# | OCT(Cl) | SPC | GDO | EtOH | WFI |
|---|---|---|---|---|---|
| 81 (91) | 3.65[1] | 43.18 | 43.18 | 10 | — |
| 82 | 2.44[2] | 43.78 | 43.78 | 10 | — |
| 83 (917) | 2.44[2] | 38.78 | 38.78 | 10 | 10 |
| 84 | 1.46[3] | 39.27 | 39.27 | 10 | 10 |

Corresponding to [1]30 mg, [2]20 mg, and [3]12 mg octreotide free base per mL when corrected for peptide purity and content and formulation density.

Example 9

Manufacturing of Formulations Containing Somatostatin 1-14 Acetate (SOM(Ac)) and Somatostatin 1-14 Hydrochloride (SOM(Cl))

Somatostatin (1-14) acetate (SOM(Ac)) and hydrochloride (SOM(Cl)) compositions according to the invention were prepared with the compositions as indicated in Table 9. The hydrochloride salt, SOM(Cl), was prepared from the acetate salt via an ion-exchange chromatography process followed by lyophilisation of the peptide solution by freeze-drying. Complete counter-ion exchange was confirmed by HPLC. The formulations were prepared by first mixing the lipid components, SPC and GDO, with the EtOH and PG components, followed by mixing on a shaking table at 250-300 rpm to form homogenous lipid solutions. To the lipid solution, the respective SOM(Ac) and SOM(Cl) drug powders were added in the required amount. The final formulations were mixed by end-over-end rotation at ambient room temperature until clear and homogenous liquid solutions were obtained. The formulations were finally subjected to sterile filtration (0.2 µm sterile PVDF filter from Millipore) under 2 bar nitrogen pressure.

TABLE 9

Composition (wt %) of somatostatin 1-14 acetate (SOM(Ac)) and somatostatin 1-14 hydrochloride (SOM(Cl)) formulations.

| Formulation# | SOM(Ac) | SOM(Cl) | SPC | GDO | EtOH | PG |
|---|---|---|---|---|---|---|
| 9 | — | 3.00 | 43.50 | 43.50 | 5 | 5 |
| 11 | — | 4.00 | 38.00 | 38.00 | 10 | 10 |
| 14 | 3.00 | — | 38.50 | 38.50 | 10 | 10 |

Example 10

In Vivo Studies of Leuprolide Formulations in Rats

For general aspects, see Example 5. Dosing of the rats was performed by subcutaneous injection of formulation 49 and 50, respectively (see Table 6).
Blood Samples for Pharmacokinetics
Blood for pharmacokinetics were collected pre-dose, and 1 hour, 4 hours, 10 hours, 1 day, 2 days, 3 days, 5 days, 7 days, 14 days and 21 days after dosing. The factual time points for sampling were calculated as the difference between time for sampling and time of dosing. A deviation of ±10% from the nominal time was accepted.
Bioanalysis
Analysis of Leuprolide was performed using the (Des-Gly10, D-LEU6, Pro-NHEt9)-LHRH (Leuprolide) high sensitivity EIA kit (S-1174, Bachem/Peninsula Laboratories) adapted for analysis of LEU in rat EDTA plasma.
Results
Pharmacokinetic (PK) profiles for formulations 49 and 50 are shown in FIG. 4.

The invention claimed is:
1. A pre-formulation consisting of a low viscosity mixture of:
  a) a lipid component consisting of:
    at least 95 wt % of:
      a1) 20-80 wt % of at least one diacyl glycerol and/or a tocopherol; and
      a2) 20-80 wt % of at least one phosphatidyl choline (PC); and
    0-5 wt % of at least one impurity associated with components a1) and/or a2);
  b) 5-15 wt % of ethanol;
  c) 5-15 wt % of propylene glycol;
  d) about 2-5 wt % of octreotide or a halide thereof or a physiologically acceptable acid thereof; and
  e) optionally 0.0008-0.1 wt % at least one antioxidant selected from the group consisting of ascorbic acid, EDTA, and citric acid;
  wherein the pre-formulation has a viscosity of 10-750 mPas at 20° C.;
  wherein the ratio of components a1:a2 is in the range 45:55 to 54:46;
  wherein components b) and c) are present in the pre-formulation in an approximately equal amount;
  wherein the pre-formulation forms, or is capable of forming, at least one liquid crystalline phase structure upon contact with excess aqueous fluid; and
  wherein the pre-formulation is for subcutaneous injection.
2. The pre-formulation as claimed in claim 1 wherein component a1) comprises glycerol dioleate (GDO).
3. The pre-formulation as claimed in claim 1 wherein component a2) comprises soy PC.
4. The pre-formulation as claimed in claim 1 wherein the antioxidant is EDTA.
5. The pre-formulation as claimed in claim 1 wherein component a1) is present at a level of 30-40% by weight.
6. The pre-formulation as claimed in claim 1 wherein component a2) is present at a level of 30-40% by weight.
7. The pre-formulation as claimed in claim 1 wherein component b) is present at a level of 6-14 wt %.
8. The pre-formulation as claimed in claim 1 wherein the ratio of components a1:a2 is in the range 47:53 to 53:47.

SEQUENCE LISTING

```
<160> NUMBER OF SEQ ID NOS: 2

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 4
<212> TYPE: PRT
<213> ORGANISM: Homo sapiens

<400> SEQUENCE: 2

Phe Trp Lys Thr
1
```

9. The pre-formulation as claimed in claim 1 wherein the ratio of components c:e is in the range 1:50 to 1:1500.

10. The pre-formulation as claimed in claim 1 wherein said pre-formulation has an $L_2$ phase structure.

11. The pre-formulation as claimed in claim 1 comprising at least one formulation from the Table below:

| Formulation | Ingredient | OCT(Cl) | SPC | GDO | EtOH | PG |
|---|---|---|---|---|---|---|
| A | (wt %) | 2.4 | 43.8 | 43.8 | 5.0 | 5.0 |
| B | (wt %) | 2.4 | 42.3 | 42.3 | 6.5 | 6.5 |

12. The pre-formulation as claimed in claim 1 wherein upon administration of said pre-formulation to a human subject, the value $C_{max}/C_{ave}$ of said peptide active agent is reduced by a factor of at least 1.2 relative to administration of a corresponding pre-formulation in which component d) is absent.

13. The pre-formulation as claimed in claim 1 wherein component c) is present at a level of 6-12 wt %.

14. The pre-formulation as claimed in claim 1 wherein component d) is octreotide, octreotide chloride, or octreotide acetate.

15. The pre-formulation as claimed in claim 1 wherein component d) is present at a level of about 2-4 wt %.

16. The pre-formulation as claimed in claim 1 wherein component e) is present.

17. The pre-formulation as claimed in claim 1 wherein component c) consists of propylene glycol, component d) is octreotide, octreotide chloride, or octreotide acetate, and component e) is present.

18. The pre-formulation as claimed in claim 17 wherein component d) is present at a level of about 2-4 wt %.

19. The pre-formulation as claimed in claim 1 wherein the lipid component a) consists of at least 99 wt % of components a1) and a2), and 0-1 wt % of at least one impurity associated with components a1) and/or a2).

20. The pre-formulation as claimed in claim 1 wherein component b) is present at a level of 8±2 wt %.

21. The pre-formulation as claimed in claim 1 wherein the ratio of components a1:a2 is in the range of about 50:50.

22. The pre-formulation as claimed in claim 1 wherein component d) is present at a level of about 3-5 wt %.

23. The pre-formulation as claimed in claim 1 wherein component d) is present at a level of about 2-3 wt %.

24. The pre-formulation as claimed in claim 1 wherein component d) is present at a level of about 2-2.5 wt %.

25. A pre-filled administration device containing the pre-formulation as claimed in claim 1.

26. The device according to claim 25 wherein said pre-formulation delivers a dosage in the range of 1 to 10 mg/week.

27. A kit comprising the administration device as claimed in claim 25.

28. A process for the formation of a pre-formulation suitable for the administration of a peptide bioactive agent to a subject, said process comprising forming a low viscosity mixture consisting of:
  a) a lipid component consisting of:
    at least 95 wt % of:
      a1) 20-80 wt % of at least one diacyl glycerol and/or a tocopherol; and
      a2) 20-80 wt % of at least one phosphatidyl choline (PC); and
    0-5 wt % of at least one impurity associated with components a1) and/or a2);
  b) 5-15 wt % of ethanol;
  c) 5-15 wt % of propylene glycol;
  d) about 2-5 wt % of octreotide or a halide thereof or a physiologically acceptable acid thereof; and
  e) optionally 0.0008-0.1 wt % at least one antioxidant selected from the group consisting of ascorbic acid, EDTA, and citric acid;
  wherein the ratio of components a1:a2 is in the range 45:55 to 54:46;
  wherein components b) and c) are present in the pre-formulation in an approximately equal amount;
  wherein component d) is dissolved or dispersed in the low viscosity mixture, or in at least one of components a1), a2), b), c) and optionally e) prior to forming the low viscosity mixture;
  wherein the pre-formulation formed has a viscosity of 10-750 mPas at 20° C.

* * * * *